(12) United States Patent
Crews et al.

(10) Patent No.: US 7,909,837 B2
(45) Date of Patent: *Mar. 22, 2011

(54) METHODS, DEVICES AND SYSTEMS FOR FORMING MAGNETIC ANASTOMOSES

(75) Inventors: Samuel Crews, Palo Alto, CA (US); J. Greg Stine, Longview, TX (US); Stephen L. Olson, Sunnyvale, CA (US); David H. Cole, San Mateo, CA (US)

(73) Assignee: Medtronic, Inc., Minneapolis, MN (US)

( * ) Notice: Subject to any disclaimer, the term of this patent is extended or adjusted under 35 U.S.C. 154(b) by 1936 days.

This patent is subject to a terminal disclaimer.

(21) Appl. No.: 10/450,989

(22) PCT Filed: Sep. 16, 2002

(86) PCT No.: PCT/US02/29485
§ 371 (c)(1),
(2), (4) Date: May 24, 2004

(87) PCT Pub. No.: WO03/024307
PCT Pub. Date: Mar. 27, 2003

(65) Prior Publication Data
US 2004/0215214 A1 Oct. 28, 2004

Related U.S. Application Data

(60) Provisional application No. 60/323,923, filed on Sep. 15, 2001.

(51) Int. Cl.
*A61B 17/08* (2006.01)
(52) U.S. Cl. ........................................................ 606/153
(58) Field of Classification Search .................. 606/153, 606/151, 155, 156, 215
See application file for complete search history.

(56) References Cited

U.S. PATENT DOCUMENTS 2,953,970 A    9/1960    Maynard
(Continued)

FOREIGN PATENT DOCUMENTS

DE    29513195    12/1996
(Continued)

OTHER PUBLICATIONS

Aharinejad S.H., et al., *Microvascular Corrosion Casting in Scanning Electron Microscopy. Technique and Applications*, Springer—Verlag/Wien, New York, pp. 12-23, 25, 28-39, 63-73, 75-81.

(Continued)

*Primary Examiner* — Darwin P Erezo
(74) *Attorney, Agent, or Firm* — Mike Jaro; Jeffrey J. Hohenshell

(57) ABSTRACT

Methods, devices and systems for forming magnetic anastomoses between two blood vessels. A first anastomotic component is removably supported by the distal end of a delivery device for attachment to a first vessel. The delivery device also supports a second anastomotic component that has been secured to a second blood vessel. The device is operated to secure the first component to the first vessel, couple the second component to the first component, and then release the components to complete the anastomosis. A robotic anastomosis system includes several robotic instruments that may be positioned through ports in a patient, used to secure an anastomotic component to a vessel, and then used to magnetically couple the components. Delivery devices for deploying magnetic anastomotic components include an actuator that uses magnetic repulsion to move the components into engagement with the inner and outer surfaces of the vessel wall. The anastomotic components are secured to the vessel wall by magnetic force and in addition may be secured by mechanical attachment.

29 Claims, 18 Drawing Sheets

U.S. PATENT DOCUMENTS

| | | | |
|---|---|---|---|
| 3,041,697 A | 7/1962 | Budreck | |
| 3,254,650 A | 6/1966 | Collito | |
| 3,254,651 A | 6/1966 | Collito | |
| 3,372,443 A | 3/1968 | Daddona, Jr. | |
| 3,519,187 A | 7/1970 | Kapitanov et al. | |
| 3,727,658 A | 4/1973 | Eldridge, Jr. | |
| 3,774,615 A | 11/1973 | Lim et al. | |
| 3,952,334 A | 4/1976 | Bokros et al. | |
| 3,986,493 A | 10/1976 | Hendren, III | |
| 4,118,806 A | 10/1978 | Porier et al. | |
| 4,154,226 A | 5/1979 | Hennig et al. | |
| 4,210,132 A | 7/1980 | Perlin | |
| 4,217,664 A | 8/1980 | Faso | |
| 4,258,705 A | 3/1981 | Sorensen et al. | |
| 4,350,160 A | 9/1982 | Kolesov et al. | |
| 4,352,358 A | 10/1982 | Angelchik | |
| 4,366,819 A | 1/1983 | Kaster | |
| 4,368,736 A | 1/1983 | Kaster | |
| 4,397,311 A | 8/1983 | Kanshin et al. | |
| 4,503,568 A | 3/1985 | Madras | |
| 4,523,592 A | 6/1985 | Daniel | |
| 4,534,761 A | 8/1985 | Raible | |
| 4,553,542 A | 11/1985 | Schenck | |
| 4,577,631 A | 3/1986 | Kreamer | |
| 4,593,693 A | 6/1986 | Schenck | |
| 4,607,637 A | 8/1986 | Berggren et al. | |
| 4,624,255 A | 11/1986 | Schenck et al. | |
| 4,624,257 A | 11/1986 | Berggren et al. | |
| 4,657,019 A | 4/1987 | Walsh et al. | |
| 4,665,906 A | 5/1987 | Jervis | |
| 4,679,546 A | 7/1987 | van Waalwijk van Doorn et al. | |
| 4,721,109 A | 1/1988 | Healey | |
| 4,747,407 A | 5/1988 | Liu et al. | |
| 4,784,646 A | 11/1988 | Feingold | |
| 4,809,713 A | 3/1989 | Grayzel | |
| 4,837,114 A | 6/1989 | Hamada et al. | |
| 4,861,330 A | 8/1989 | Voss | |
| 4,889,120 A | 12/1989 | Gordon | |
| 4,899,744 A | 2/1990 | Fujitsuka et al. | |
| 4,904,256 A | 2/1990 | Yamaguchi | |
| 4,907,591 A | 3/1990 | Vasconcellos et al. | |
| 4,917,087 A | 4/1990 | Walsh | |
| 4,917,090 A | 4/1990 | Berggren et al. | |
| 4,917,091 A | 4/1990 | Berggren et al. | |
| 4,917,778 A | 4/1990 | Takada et al. | |
| 4,935,080 A | 6/1990 | Hassell et al. | |
| 5,013,411 A | 5/1991 | Minowa et al. | |
| 5,015,238 A | 5/1991 | Solomon et al. | |
| 5,089,006 A | 2/1992 | Stiles | |
| 5,119,983 A | 6/1992 | Green et al. | |
| 5,156,619 A | 10/1992 | Ehrenfeld | |
| 5,178,634 A | 1/1993 | Martinez | |
| 5,192,289 A | 3/1993 | Jessen | |
| 5,211,683 A | 5/1993 | Maginot | |
| 5,217,474 A | 6/1993 | Zacca et al. | |
| 5,234,447 A | 8/1993 | Kaster et al. | |
| 5,250,060 A | 10/1993 | Carbo et al. | |
| 5,275,891 A | 1/1994 | Tagaya et al. | |
| 5,304,220 A | 4/1994 | Maginot | |
| 5,314,468 A | 5/1994 | Martinez | |
| 5,316,595 A | 5/1994 | Hamada et al. | |
| 5,330,486 A | 7/1994 | Wilk | |
| 5,336,233 A | 8/1994 | Chen | |
| 5,366,462 A | 11/1994 | Kaster et al. | |
| 5,395,311 A | 3/1995 | Andrews | |
| 5,411,508 A | 5/1995 | Bessler et al. | |
| 5,425,763 A | 6/1995 | Stemmann | |
| 5,441,507 A | 8/1995 | Wilk | |
| 5,443,497 A | 8/1995 | Venbrux | |
| 5,456,712 A | 10/1995 | Maginot | |
| 5,456,714 A | 10/1995 | Owen | |
| 5,464,449 A | 11/1995 | Ryan et al. | |
| 5,478,354 A | 12/1995 | Tovey et al. | |
| 5,507,629 A | 4/1996 | Jarvik | |
| 5,522,834 A | 6/1996 | Fonger et al. | |
| 5,556,405 A | 9/1996 | Lary | |
| 5,571,167 A | 11/1996 | Maginot | |
| 5,595,562 A * | 1/1997 | Grier | 600/12 |
| 5,611,689 A | 3/1997 | Stemmann | |
| 5,626,601 A | 5/1997 | Gershony et al. | |
| 5,643,340 A | 7/1997 | Nunokawa | |
| 5,669,918 A | 9/1997 | Balazs et al. | |
| 5,676,670 A | 10/1997 | Kim | |
| 5,681,260 A | 10/1997 | Ueda et al. | |
| 5,690,656 A | 11/1997 | Cope et al. | |
| 5,693,088 A | 12/1997 | Lazarus | |
| 5,695,504 A * | 12/1997 | Gifford et al. | 606/153 |
| 5,697,943 A * | 12/1997 | Sauer et al. | 606/153 |
| 5,702,412 A | 12/1997 | Popov et al. | |
| 5,707,362 A | 1/1998 | Yoon | |
| 5,707,380 A | 1/1998 | Hinchliffe et al. | |
| 5,725,544 A | 3/1998 | Rygaard | |
| 5,725,553 A | 3/1998 | Moenning | |
| 5,758,663 A | 6/1998 | Wilk et al. | |
| 5,797,920 A | 8/1998 | Kim | |
| 5,817,113 A | 10/1998 | Gifford, III et al. | |
| 5,830,224 A | 11/1998 | Cohn et al. | |
| 5,868,763 A | 2/1999 | Spence et al. | |
| 5,895,404 A | 4/1999 | Ruiz | |
| 5,904,147 A | 5/1999 | Conlan et al. | |
| 5,906,579 A | 5/1999 | Vander Salm et al. | |
| 5,916,226 A | 6/1999 | Tozzi | |
| 5,968,089 A | 10/1999 | Krajicek | |
| 5,997,467 A | 12/1999 | Connolly | |
| 6,056,762 A * | 5/2000 | Nash et al. | 606/153 |
| 6,068,637 A | 5/2000 | Popov et al. | |
| 6,074,416 A | 6/2000 | Berg et al. | |
| 6,099,542 A | 8/2000 | Cohn et al. | |
| 6,113,612 A | 9/2000 | Swanson et al. | |
| 6,152,937 A | 11/2000 | Peterson et al. | |
| 6,173,715 B1 | 1/2001 | Sinanan et al. | |
| 6,179,849 B1 | 1/2001 | Yencho et al. | |
| 6,187,020 B1 | 2/2001 | Zegdi et al. | |
| 6,190,353 B1 | 2/2001 | Makower et al. | |
| 6,206,913 B1 | 3/2001 | Yencho et al. | |
| 6,241,743 B1 | 6/2001 | Levin et al. | |
| 6,293,955 B1 | 9/2001 | Houser et al. | |
| 6,296,604 B1 | 10/2001 | Garibaldi et al. | |
| 6,350,280 B1 * | 2/2002 | Nash et al. | 623/1.36 |
| 6,352,543 B1 * | 3/2002 | Cole | 606/153 |
| 6,419,681 B1 | 7/2002 | Vargas et al. | |
| 6,428,550 B1 | 8/2002 | Vargas et al. | |
| 6,491,705 B2 | 12/2002 | Gifford, III et al. | |
| 6,558,400 B2 | 5/2003 | Deem et al. | |
| 6,565,581 B1 | 5/2003 | Spence et al. | |
| 6,575,168 B2 | 6/2003 | LaFontaine et al. | |
| 6,579,311 B1 | 6/2003 | Makower | |
| 6,616,675 B1 | 9/2003 | Evard et al. | |
| 6,632,229 B1 | 10/2003 | Yamanouchi | |
| 6,652,540 B1 * | 11/2003 | Cole et al. | 606/153 |
| 6,719,768 B1 * | 4/2004 | Cole et al. | 606/153 |
| 6,802,847 B1 * | 10/2004 | Carson et al. | 606/153 |
| 6,932,827 B2 * | 8/2005 | Cole | 606/153 |
| 7,214,234 B2 | 5/2007 | Rapacki et al. | |
| 7,232,449 B2 * | 6/2007 | Sharkawy et al. | 606/153 |
| 7,241,300 B2 | 7/2007 | Sharkawy et al. | |
| 2002/0143347 A1 | 10/2002 | Cole et al. | |
| 2002/0193782 A1 | 12/2002 | Ellis et al. | |
| 2003/0014061 A1 | 1/2003 | Houser et al. | |
| 2003/0014063 A1 | 1/2003 | Houser et al. | |
| 2003/0065345 A1 | 4/2003 | Weadock | |
| 2003/0167064 A1 | 9/2003 | Whayne | |
| 2004/0215214 A1 | 10/2004 | Crews | |
| 2005/0021059 A1 | 1/2005 | Cole | |
| 2005/0080439 A1 | 4/2005 | Carson | |
| 2005/0192603 A1 | 9/2005 | Cole | |
| 2006/0161244 A1 | 7/2006 | Seguin | |
| 2006/0282106 A1 | 12/2006 | Cole | |
| 2007/0010834 A1 | 1/2007 | Sharkawy | |
| 2007/0250084 A1 | 10/2007 | Sharkawy | |

FOREIGN PATENT DOCUMENTS

| | | |
|---|---|---|
| DE | 29713335 | 7/1997 |
| FR | 2760627 | 9/1998 |
| RU | 2018266 | 3/1989 |
| RU | 2123300 | 12/1998 |
| SU | 736966 | 5/1980 |

| | | |
|---|---|---|
| SU | 1025420 | 6/1983 |
| SU | 1179978 | 9/1985 |
| SU | 1438738 | 11/1988 |
| SU | 1537228 | 1/1990 |
| SU | 1595534 | 9/1990 |
| SU | 1629040 | 2/1991 |
| SU | 1635966 | 3/1991 |
| SU | 1277452 | 6/1991 |
| SU | 1708313 | 1/1992 |
| SU | 1361753 | 4/1992 |
| SU | 1725851 | 4/1992 |
| SU | 1766383 | 10/1992 |
| SU | 1769863 | 10/1992 |
| WO | WO 81/00668 | 3/1981 |
| WO | WO 97/31578 | 2/1996 |
| WO | WO 97/12555 | 4/1997 |
| WO | WO 97/13463 | 4/1997 |
| WO | WO 97/27897 | 8/1997 |
| WO | WO 98/40036 | 9/1998 |
| WO | WO 99/40851 | 8/1999 |
| WO | WO 99/62415 | 12/1999 |
| WO | WO 99/63894 | 12/1999 |
| WO | WO 00/09040 | 2/2000 |
| WO | WO 00/24339 | 5/2000 |
| WO | WO 00/27312 | 5/2000 |
| WO | WO 00/32241 | 6/2000 |
| WO | WO 00/33770 | 6/2000 |
| WO | WO 00/69364 | 11/2000 |
| WO | WO 00/74579 | 12/2000 |
| WO | WO 01/39672 | 6/2001 |
| WO | WO 01/82803 | 11/2001 |
| WO | WO 02/09594 | 2/2002 |
| WO | WO 02/19946 | 3/2002 |
| WO | WO 02/39878 | 5/2002 |
| WO | WO 02/094108 | 11/2002 |

OTHER PUBLICATIONS

Ahn CY, Shaw WW, Berns S, et al., "Clinical Experience With the 3M Microvascular Coupling Anastomotic Device in 100 Free-Tissue Transfers," *Plastic and Reconstructive Surgery*, Jun. 1994; 93(7):1481-84.

Angelini E, et al., "Corrosion under Static and Dynamic Conditions of Alloys Used for Magnetic Retention in Dentistry," *J Prosthet Dent*, 1991; 65:848-53.

ASM Metals Reference Book, Third Edition, Copyright 1993, p. 355.

Attai, et al., *Aortic Valve Replacement in the Presence of Hufnagel Valve in the Descending Aorta*, J. Thoracic Cardiovas. Surg., 1974, 68(1):112-115.

Attanasio SA, et al., "Corrosion of Rapidly Solidified Neodymion-Iron-Boron (Nd-Fe-B) Permanent Magnets and Protection via Sacrificial Zinc Coatings," *Material Science and Engineering*, 1995; A198:25-34.

Bala H, et al., "Effect of Impurities on the Corrosion Behavior of Neomydium," *Journal of Applied Electrochemistry*, 1993; 23(10):1017-1024.

Beppu, et al., *A Computerized Control System for Cardiopulmonary Bypass*, J. Thoracic Cardiovas. Surg., 1995, 109(3):428-438.

Bjork VO, Iert T, Landou C., "Angiographic changes in Internal Mammary Artery and Saphenous Vein Grafts, Two Weeks, One Year and Five Years After Coronary Bypass Surgery," *Scand J Thor Cardiovasc Surg*, 1981; 15:23-30.

Bondemark, et al., "Long-term effects of orthodontic magnets on human buccal mucosa—a clinical, histological and immunohistochemical study," *Eur J Orthod*, 20(3): Jun. 1998, pp. 211-218.

Bondemark, et al., "Orthodontic Rare Earth Magnets—In Vitro Assessment of Cytotoxicity," *British Journal of Orthodontia*, vol. 21, No. 4, Nov. 1994, pp. 335-341.

Bornemisza G, Furka I., "Nonsuture Vascular Anastomosis," *Acta Chirurgica Academiae Scientiarium Hungaricae, Tomus*, 1971; 12(1):49-56.

Bourassa MG, Fisher LD, Campeau L, et al., "Long-Term Fate if Bypass Grafts: The Coronary Artery Surgery Study (CASS) and Montreal Heart Institute Experiences," *Circ*, Dec. 1985; 72(suppl V):71-77.

Brochure for "Neomax, Rare Earth Magnets," pp. 31-33, undated.

Buffolo E, de Andrade JCS, Branco JNR, et al., "Coronary Artery Bypass Grafting Without Cardiopulmonary Bypass," *Ann Thorac Surg*, 1996; 61:63-6.

Casanova R, Herrera GA, Vasconez EB, et al., "Microarterial Sutureless Sleeve Anastomosis Using a Polymeric Adhesive: An Experimental Study," *J Reconstr Microsurg*, Apr. 1987; 3(3):201-7.

Cha, et al., *Silent Coronary Artery-Left Ventricular Fistula: A Disorder of the Thebesian System?*, Angiology, 1978; 29(2):169-173.

Cheng CW, Cheng FT, Man HC, "Improvement of protective coatings on Nd-Fe-B magnet by pulse nickel plating," *Journal of Applied Physics*, Jun. 1, 1998; 83(11):6417-6419.

Cheng CW, et al., "Magnetic and Corrosion Characteristics of Nd-Fe-B Magnet with Various Surface Coatings," *IEEE Transactions on Magnetics*, 1997; 33(5):3910-3912 and CD-10.

Cope, "Creation of Compression Gastroenterostomy by Means of the Oral, Percutaneous, or Surgical Introduction of Magnets: Feasibility Study in Swine," *Journal of Vascular and Interventional Radiology*, vol. 6, No. 4, Jul.-Aug. 1995, pp. 539-545.

Cope, "Evaluation of Compression of Cholecystogastric and Cholecystojejunal Anastomoses in Swine after Peroral and Surgical Introduction of Magnets," *Journal of Vascular and Interventional Radiology*, vol. 6, No. 4, Jul.-Aug. 1995, pp. 546-552.

Cope, "Stent Placement of Gastroenteric Anastomoses Formed by Magnetic Compression," *Journal of Visceral Intervention*, vol. 10, No. 10, Nov.-Dec. 1999, pp. 1379-1386.

Dake, et al., *Transluminal Placement of Endovascular Stent-Grafts for the Treatment of Descending Thoracic Aortic Aneurysms*, New England J. Med., 1994, 331(2):1729-1.

David JL, Limet R, "Antiplatelet Activity of Clopidogrel in Coronary Artery Bypass Graft Surgery Patients," *Thromb Haemost*, Nov. 1999; 82(5):417-21.

DeLacure MD, Kuriakose MA, Spies AL, "Clinical Experience in End-to-Side Venous Anastomosis With a Microvascular Anastomotic Coupling Device in Head and Neck Reconstruction," *Arch Otolaryngol Head Neck Surg*, Aug. 1999; 125:869-72.

Detweiler MB, Detweiler JG, Fenton J, et al., "Sutureless and Reduced Suture Anastomosis of Hollow Vessels with Fibrin Glue: A Review," *J Invest Surg*, Sep. 1999; 12(5):245-62.

Dormer KJ, Gan RZ, Santo R, "Middle Ear Titanium Transducer," *Society for Biomaterials*, Sixth World Biomaterials Congress Transactions; 2000: 1272.

Eckstein FS, Bonilla LF, Meyer B, et al., "Sutureless mechanical anastomosis of a saphenous vein graft to a coronary artery with a new connector device," *Lancet*, vol. 357, Mar. 24, 2001, pp. 931-932.

Endo K, et al., "Effects of Titanium Nitride Coatings on Surface and Corrosion Characteristics on Ni-Ti Alloy," *Dental Materials Journal*, 1994; 13(2):228-39.

Esformes, et al., "Biological Effects of Magnetic Fields Generated with CoSm Magnets," *Bull Hosp Jt Dis Orthop Inst*, 1981; 41 pp. 81-87.

Evans RD, et al., "Effect of Corrosion Products (neodymium Iron Boron) on Oral Fibroblast Proliferation," *J of Applied Biomater*, 1995; 6(3):199-202.

Frey RR, Bruschke AVG, Vermeulen FEE, "Serial Angiographic Evaluation 1 Year and 9 Years After Aorata-Coronary Bypass," *J Thorac Cardiovasc Surg*, 1984; 87(2):167-74.

Fuestel, et al., "Kontinente Kolostomie durch Magnetverschluss," *Dtsch. Med. Wschr.* 100 (1975), pp. 1063-1064 (includes English Abstract).

Fukumura, et al., "Development of a Magnetically Operated Artificial Urethral Sphincter," *ASAIO Journal*, 1993, pp. M283-M287.

Goldman S, Copeland J, Moritz T, et al., "Improvement in Early Saphenous Vein Graft Patency After Coronary Artery Bypass Surgery With Antiplatelet Therapy: Results of a Veterans Administration Cooperative Study," *Circulation*, Jun. 1988; 77(6):1324-32.

Goldman S, et al., "Starting aspirin therapy after operation—effects on early graft patency," *Circulation*, 1991; 84:520-526.

Goldman S, Zadina K, Krasnicka B, et al., "Predictors of Graft Patency 3 Years After Coronary Artery Bypass Graft Surgery," *J Am Coll Cardiol*, Jun. 1997; 29(7):1563-8.

Goy JJ, Kaufman U, Goy-Eggenberger D, et al., "A Prospective Randomized Trial Comparing Stenting to Internal Mammary Artery Grafting for Proximal, Isolated de novo Left Anterior Coronary Artery Stenosis: The SIMA Trial, Stenting vs. Internal Mammary Artery," *Mayo Clin Proc*, Nov. 2000; 75(11):1116-23.

Grieb B, "New Corrosion Resistant Materials Based on Neodym-Iron-Boron," *Intermag Conference*, 1997; CD-08.

Group Arnold, The Magnetic Products Group of SPS Technologies, "Neodymium Magnets," Website: www.grouparnold.com, 4 pages (2008).

Gundry SR, Black K, Izuntani H, "Sutureless Coronary Artery Bypass with Biologic Glued Anastomosis: Preliminary In Vivo and In Vitro Results," *J Thorac Cardiovasc Surg*, Sep. 2000; 120(3):473-77.

Guyton RA, McClenathan JH, Michaelis LL, "A Mechanical Device for Sutureless Aorta-Saphenous Vein Anastomosis," *Ann Thorac Surg*, Oct. 1979; 28(4):342-5.

Heijmen RH, Borst C, van Dalen R, et al., "Temporary Luminal Arteriotomy Seal: II. Coronary Artery Bypass Grafting on the Beating Heart," *Ann Thorac Surg*, 1998; 66:471-6.

Heijmen RH, Hinchliffe P, Borst C, et al., "A Novel One-Shot Anastomotic Stapler Prototype for the Coronary Bypass Grafting on the Beating Heart: Feasibility on the Pig," *J Thorac and Cardiovasc Surg*, Jan. 1999; 117(1):117-25.

Ilia, R., Coronary Angiography in Dextrocardia, *Catheterization Cardio. Diag*., 1991, 24 p. 150.

Jamieson, S.W., *Aortocoronary Saphenous Vein Bypass Grafting*, Operative Surgery, 4th Edition, pp. 454-470.

Jansen, et al., "Clinical Applications of Magnetic Rings in Colorectal Anastomosis," *Surgery, Gynecology & Obstetrics*, vol. 153, Oct. 1981, pp. 537-545.

Kajiya, et al., *Mechanical Control of Coronary Arter Inflow and Vein Outflow*, Jap. Cir. J., 1989, 53:431-438.

Kanshin, et al., "A Goal-Oriented Local Approach to the Prevention of Postoperative Purulent Complications," 1991, pp. 24-27 (English abstract is provided).

Kanshin, et al., "Sutureless anastomoses in gastrointestinal surgery with and without steady magnetic field," *Arkh Patol*, 1978; 40(8):56-61 (with English Abstract).

Kitsugi A, et al., "The Corrosion Behavior of Nd2Fe14B and SmCo5 Magnets," *Dental Materials Journal*, 1992; 11(2):119-29.

Konerding MA, et al., "Scanning Electron Microscopy of Corrosion Casting in Medicine," *Scanning Microscopy*, 1991; 5(3):851-865.

Ku NC, et al., "Enhanced corrosion Resistance of NdFeB Type Permanent Magnet Coated by a Dual Layer of Either Ti/Al or Ni/Al Intermetallics," *IEEE Transactions on Magnetics*, 1997; 33(5):3913-5.

Ku NC, Qin C-D, Yu CC and Ng DHL, "Corrosion Reisstance of NdFeB magnets coated by Al," *IEEE Transactions on Magnetics*, Sep. 1996; 32(5):4407-4409.

Lamestschwandter A, et al., "Scanning Electron Microscopy of Vascular Corrosion Casts—Technique and Applications: Updated Review," *Scanning Microscopy*, 1990; 4(4):889-941.

Louagie, et al., *Operative Risk Assessment in Coronary Artery Bypass Surgery, 1990-1993: Evaluation of Perioperative Variables*, Thorac. Cardiovasc. Surg., 1995, 43:134-141.

Lytle BW, Loop FD, Cosgrove DM, et al., "Long-Term (5 to 12 Years) Serial Studies of Internal Mammary Artery and Saphenous Vein Coronary Bypass Grafts." *J Thorac and Cardiovasc Surg*, Feb. 1985; 89(2):248-58.

Magnet Sales and Manufacturing Company, Inc., "Neodymium Iron Boron," Website: www.magnetsales.com, 4 pages (2008).

Mattox DE, Wozniak JJ, "Sutureless Vascular Anastomosis with Biocompatible Heat-Shrink Tubing," *Arch Otolaryngol Head Neck Surg*, Nov. 1991; 117:1260-4.

Minowa T, Yoshikawa M, Honshima M, "Improvement of the corrosion resistance on Nd-Fe-B magnet with nickel plating," *IEEE Transactions on Magnetics*, Sep. 1989; 25(5):3776-3778.

Myshkin, et al., "Use of Permanent Magnets in Sutureless Anastomoses," 1987, pp. 47-52 (English translation is provided).

Nataf P, Hinchliffe P, Manzo S, et al., "Facilitated Vascular Anastomoses: The One-Shot Device," *Ann Thorac Surg*, 1998; 66:1041-4.

Nataf P, Kirsch W, Hill AC, et al., "Nonpentrating Clips for Coronary Anastomosis," *Ann Thorac Surg*, 1997; 63:S135-7.

Noar JH, Whab A, Evans RD, Wojcik AG, "The durability of parylene coatings on neodymium-iron-boron magnets," *Eur J Orthod*,, Dec. 1999; 21(6):685-93.

Obora, et al., "Nonsuture Microvascular Anastomosis Using Magnet Rings: Preliminary Report," *Surg. Neurol.*, vol. 9, Feb. 1978, pp. 117-120.

Obora, et al., "Nonsuture Microvascular Anastomosis using Magnetic Rings," *Neurol Med Chir* May 20, 1980, (5) pp. 497-505. (English translation is provided.).

Paz MA, Lupon J, Bosch X, et al., "Predictors of Early Saphenous Vein Aortocoronary Bypass Graft Occlusion. The GESIC Study Group," *Ann Thorac Surg*, Nov. 1993; 56(5):1101-6.

Pirusyan, et al., "Some Regularities of Tissue Squeezing and Regeneration Under Formation of "unstitch" Anastomoses of the Alimentary Canal's Hollow Organs," 1979, pp. 13-17 (includes English abstract).

Pourbaix M, "Electrochemical Corrosion of Metallic Biomaterials," *Biomaterials*, 1984; 5:122-34.

Puskas JD, Wright CE, Ronson RS, et al., "Clinical Outcomes and Angiographic Patency in 125 Consecutive Off-Pump Coronary Bypass Patients," *The Heart Surgery Forum #999-95310*, May 1999; 2(3):216-21.

Reddy, et al., *Multiple Coronary Arteriosystemic Fistulas*, Amer. J. Cardiol., 1974, 33:304-306.

Riess, Friedrich-Christian, et al., "Clinical Experience with the CorLink Device for Proximal Anastomosis of the Saphenous Vein to the Aorata: A Clinical Prospective, and Randomized Study," *The Heart Surgery Forum*, #2002-71002, 5(4), 2002:345-353.

Rueland D, Schomacher PR, Mueller KM, et al., "Experimental Studies With a New Sutureless Anastomic Flange," *Trans AM Soc Artif Intern Organs*, 1979; 25:339-43.

Ryhanen J, et al., "Biocompatibility of Nickel-Titanium Shape Memory Metal and Its Corrosion Behavior in Human Cell Cultures," *JBMR*, 33 1997; 451-7.

Sanz G, Pajaron A, Algria E, et al., "Prevention of Early Aortocoronary Bypass Occlusion by Low-Dose Aspirin and Dipyridamole," *Circulation*, Sep. 1990; 82(3):765-73.

Sastri, et al., *Coronary Artery Left Ventricular Fistula*, Chest, 1975, 68(5):735-736.

Scheltes JS, Heikens M, Pistecky PV, et al., "Assessment of Patented Coronary End-to-Side Anastomotic Devices Using Micromechanical Bonding," *Ann Thorac Surg*, Jul. 2000; 70(1):218-21.

Segal, et al., *Alterations of Phasic Coronary Artery Flow Velocity in Humans During Percutaneous Coronary Angioplasty*, JACC, 1992, 20(2):276-286.

Seides SF, Borer JS, Kent KM, et al., "Long-Term Anatomic Fate of Coronary-Artery Bypass Grafts and Functional Status of Patients Five Years after Operation," *N. Engl J Med*, 1978; 298(22):1213-17.

Senftle F, et al., "Electrolytic Corrosion of Gold and the Formation of Au2(SO4)3 in Concentrated Sulfuric Acid," *Journal of the Electrochemical Society*, 1985; 129-30.

Sethi GK, Copeland JG, Goldman S, et al., "Implications of Preoperative Administration of Aspirin in Patients Undergoing Coronary Artery Bypass Grafting. Department of Veterans Affairs Cooperative Study on Antiplatelet Therapy," *J Am Coll Cardiol*, Jan. 1990; 15(1):15-20.

Souza DSR, Bomfim V, Skoglund H, et al., "High Early Patency Saphenous Vein Graft for Coronary Artery Bypass Havested with Surrounding Tissue," *Ann Thorac Surg*, 2001; 71:797-800.

Stepanov, et al., "The treatment of intestinal fistulae in children by applying a by-pass anastomosis using magnetic devices," *Khirugiia (Mosk)*, Nov.-Dec. 1992, pp. 11-12 (English abstract is provided).

Stevens, et al., Port-Access Coronary Artery Bypass Grafting: A Proposed Surgical Method, J. Thorac. *J. Cardiovasc. Surg.*, 1996, 111(3):567-573.

Sugiura T., "Magnetic Compression Anastomosis of the Vascular System in Experimental Dog Models," 211, p. S141, 1 page English abstract and 12 page slide show.

Supplementary Partial European Search Report from European Patent Application No. 01959718.6 dated Jan. 7, 2005.

Takenaka H, Esato K, Ohara M, et al., "Sutureless Anastomosis of Blood Vessels Using Cyanoacrylate Adhesives," *Surg Today*, 1992; 22(1):46-54.

Thierry B, et al., "Effect of Surface Treatment and Sterilization Processes on the Corrosion Behavior of NiTi Shape Memory Alloy," *JBMR*, 51(4), 2000; 685-93.

von Segesser, L.K., *Arterial Grafting for Myocardial Revascularization*, 1990, pp. 3-140.

Weissberg D, Schwartz P, Goetz RH, Nonsuture End-to-Side Anastomoses of Small Blood Vessels, *Surgery, Gynecology & Obstetrics*, Aug. 1966; 341-46.

Werker P, Kon M, "Review of Facilitated approaches to Vascular Anastomosis Surgery," *Ann Thorac Surg*, 1997; 63:S122-7.

Whiffen JD, Boake WC, Gott VL, "Vessel Patency Following Nonsuture Anastomosis with Intravascular Rings," *Arch Surg*, Dec. 1965; 91(6):939-41.

Willman CJ, et al., "Corrosion Characteristics of RE-Fe-B Permanent Magnets," *J Appl Phys*, 1987; 61(8):3766-3768.

Yamagata S, Carter LP, Handa H, et al., "Experimental Studies in Nonsuture End-to-Side Microvascular Anastomosis," *Neurol Med Chiro* (Tokyo), 1981; 21:701-08.

Yanase, "An Experimental Study on Traumatic Changes in Microvessels Produced by Pressure Clamping," *Aust N. Z. J. Surg*, vol. 50-No. 4, Aug. 1980, pp. 423-428.

Zegdi R, Martinod E, Fabre O, et al., "Video-Assisted Replacement of Bypass Grafting of the Descending Thoracic Aorta With a New Sutureless Vascular Prostahesis: An Experimental Study," *J Vasc Surg*, 1999; 30:320-4.

* cited by examiner

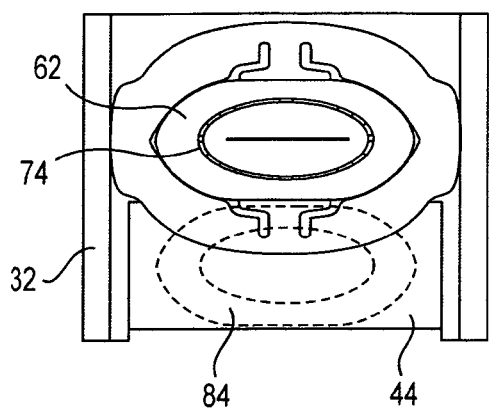
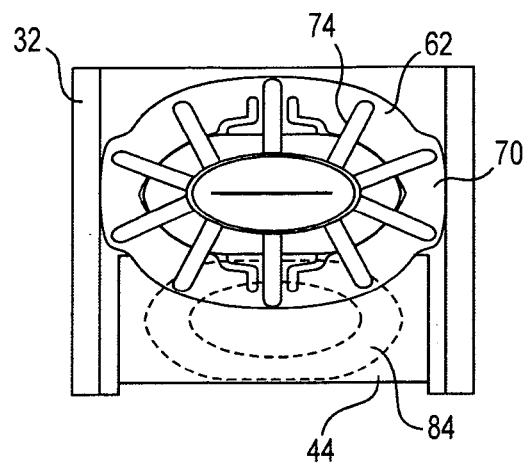
Fig. 7A    Fig. 7B
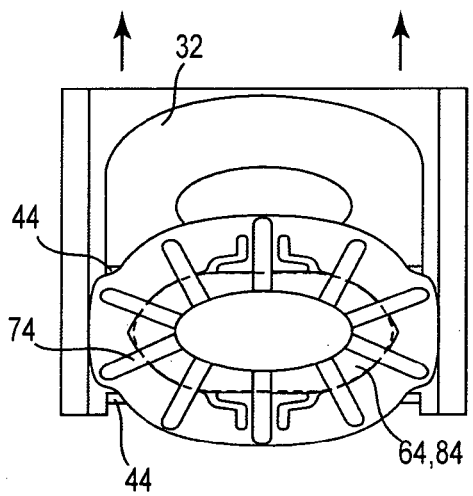
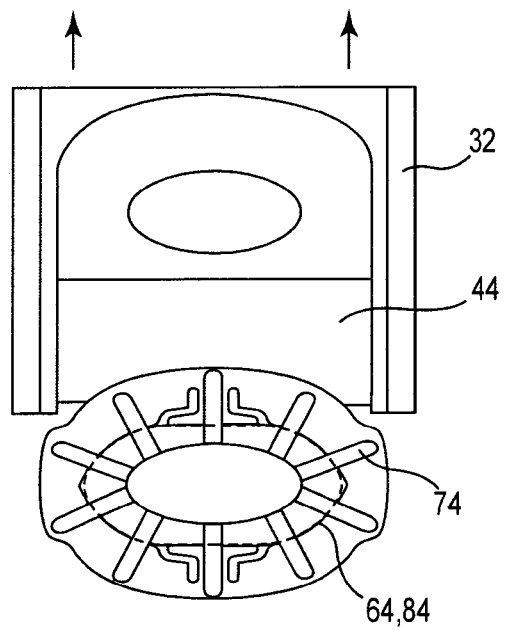
Fig. 7C    Fig. 7D

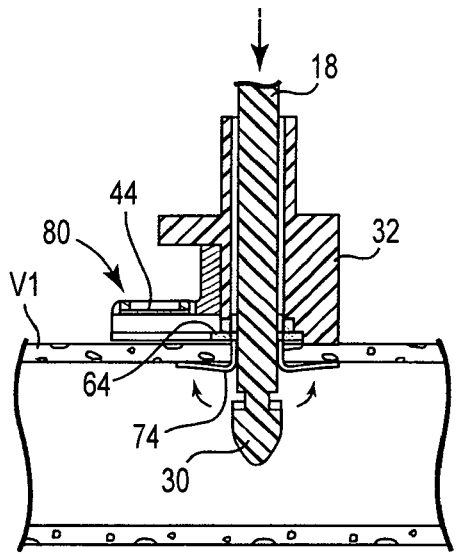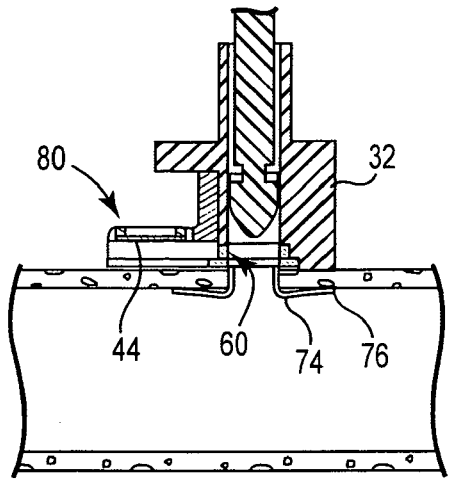
Fig. 8A  Fig. 8B
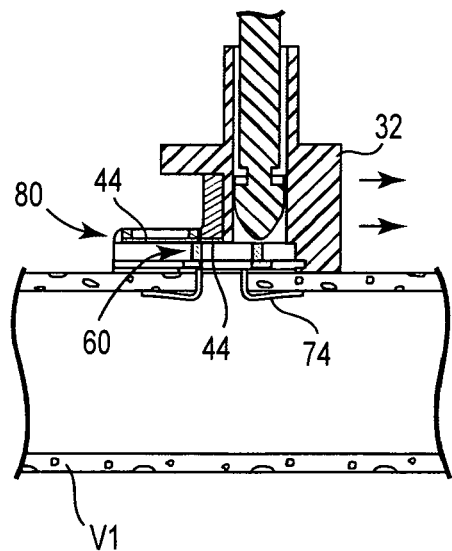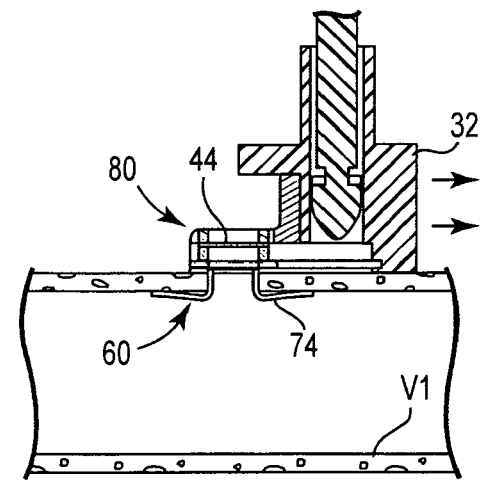
Fig. 8C  Fig. 8D

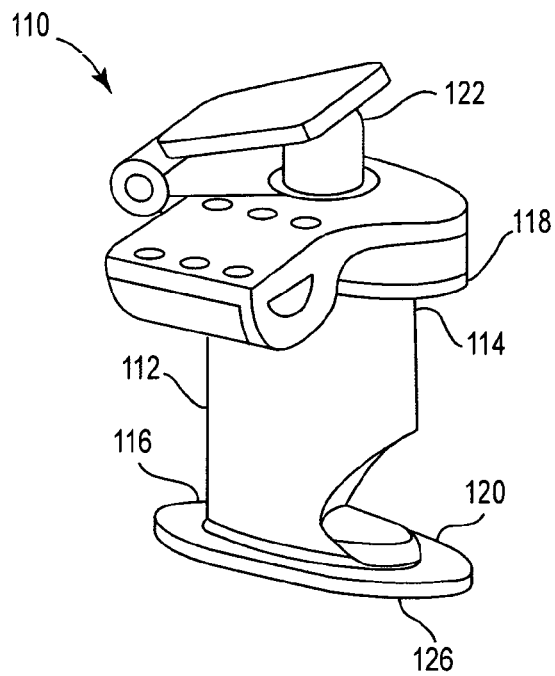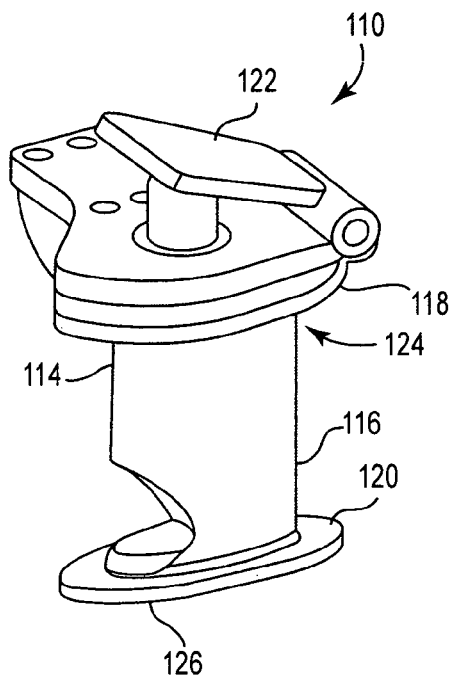
Fig. 10A  Fig. 10B
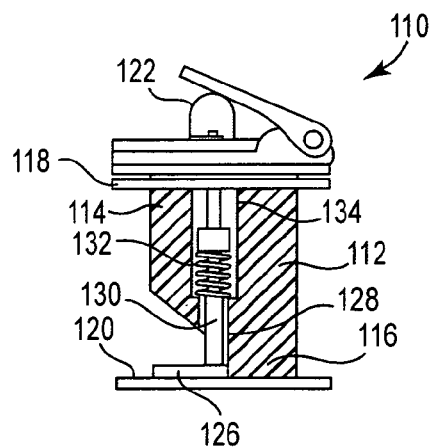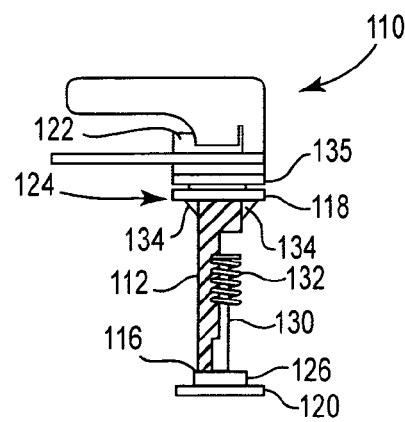
Fig. 11A  Fig. 11B

METHODS, DEVICES AND SYSTEMS FOR FORMING MAGNETIC ANASTOMOSES

CROSS-REFERENCE TO RELATED APPLICATIONS

The present application claims priority under 35 USC §119 (e) from provisional application Ser. No. 60/323,923, filed Sep. 15, 2001. This application also claims priority under 35 USC §120 from the following applications: application Ser. No. 10/022,187, filed Dec. 13, 2001, application Ser. No. 09/915,226, filed Jul. 23, 2001, application Ser. No. 09/851,400, filed May 7, 2001, application Ser. No. 09/638,805, filed Aug. 12, 2000, and application Ser. No. 09/562,599, filed Apr. 29, 2000, now U.S. Pat. No. 6,352,543. The entire disclosure of each of the above-referenced patent applications is expressly incorporated herein by reference.

BACKGROUND OF THE INVENTION

1. Field of the Invention

The invention relates to forming an anastomoses between hollow anatomical structures or bodies, such as blood vessels, and more particularly, to using magnetism to form such anastomoses.

2. Description of Related Art

Many anastomotic couplings have been proposed as substitutes for a conventional, handsewn sutured anastomosis; they have had limited success. Such couplings are used to attach various hollow structures in the body, including blood vessels. In the vascular field, most of the proposed couplers or connectors have failed to duplicate the success of sutured anastomoses and, as such, have not been widely used or accepted.

Among the drawbacks associated with proposed anastomotic couplers are failure to achieve an acceptable patency rate, insecure or inadequate attachment of the coupler to the vessels, and the inability to produce a good anastomosis on a repeated basis.

Accordingly, there is a need in the art for methods and devices for forming a non-sutured anastomosis between hollow bodies in a quick, easy and repeatable manner.

SUMMARY OF THE INVENTION

According to one embodiment, the invention provides a method for forming an anastomosis between first and second hollow bodies using magnetic force. The method includes steps of providing first and second anastomotic components that are magnetically attracted to each other and are configured to be secured to first and second hollow bodies. The first component is mounted on a delivery device while the second anastomotic component is secured to the second hollow body and then mounted on the delivery device. The first anastomotic component is secured to the first hollow body, and magnetism is used to couple the first and second anastomotic components and form an anastomosis between the first and second hollow bodies.

Another embodiment provides a method for coupling first and second magnetically attracted anastomotic components mounted on a delivery device and includes steps of providing a delivery device configured to support the anastomotic components, mounting the first component on the delivery device, and mounting the second component on the delivery device in a first position. The second component is moved to a second position and magnetism is used to couple the components.

Another embodiment provides a method for bypassing a portion of a blood vessel using magnetism. The method has steps of providing first and second anastomotic components that are magnetically attracted, respectively, to third and fourth anastomotic components, providing a graft vessel having a proximal portion adapted to be secured to a source of blood and a distal portion adapted to be secured to a target vessel so as to bypass a portion of the target vessel. Additional steps include securing the first anastomotic component to the proximal portion of the graft vessel, securing the second anastomotic component to the distal portion of the graft vessel, securing the third anastomotic component to a source of blood and securing the fourth anastomotic component to the target vessel at a location distal to the portion to be bypassed. Further steps include using magnetism to couple the first and third anastomotic components together and form a proximal anastomosis, after using magnetism to couple the second and fourth anastomotic components together to form a distal anastomosis.

Another embodiment provides a method for forming an anastomosis between first and second hollow bodies using magnetic force and includes steps of positioning a first anastomotic component on a delivery device, the first anastomotic component adapted to be secured to a first hollow body, positioning a second anastomotic component on the delivery device, the second anastomotic component adapted to be secured to a second hollow body, wherein the first and second anastomotic components are magnetically attracted to each other and are positioned on the delivery device in an offset configuration with respect to one another. Additional steps include securing the second anastomotic component to a second hollow body so as to place the opening of the second component in communication with the second hollow body, moving the first and second anastomotic components from the offset configuration into substantial alignment with each other, and using magnetism to couple the first and second anastomotic components and form an anastomosis between the first and second hollow bodies.

Another embodiment of the invention provides a system for forming a magnetic anastomosis between first and second hollow bodies. The system includes a delivery device and first and second anastomotic components that are magnetically attracted to one another, the components being mounted on the delivery device in a first orientation, preferably in alignment with each other. A transfer member moves at least one of the first and second anastomotic components to place the components in a second relative orientation in which they are aligned.

Still another embodiment of the invention provides a system for forming a magnetic anastomosis between first and second hollow bodies. The system includes a delivery device and first and second anastomotic components that are magnetically attracted to one another. The first and second anastomotic components are supported by the delivery device so as to be physically unconnected, and an actuator is used to deliver the first and second components and create a magnetic anastomosis between the two hollow bodies.

Another embodiment of the invention provides a method using robotics to form a magnetic anastomosis between first and second hollow bodies. The method includes steps of providing first and second anastomotic components respectively configured to be secured to first and second hollow bodies, the first and second components being magnetically attracted to one another, using a robotic element to secure the first anastomotic component to the first hollow body, using a robotic element to secure the second anastomotic component to the second hollow body, and coupling the first and second anastomotic components via magnetic force to form an anastomosis between the first and second hollow bodies.

Still another embodiment of the invention provides a robotic system for forming an anastomosis between first and second hollow bodies using magnetic force. The system includes multiple robotic elements configured to removably support first and second anastomotic components respectively configured to be secured to first and second hollow bodies, the first and second components being magnetically attracted to one another. The first and second anastomotic components are supported by the robotic elements and a user may operate the robotic system to manipulate the robotic elements to secure the first and second anastomotic components to the first and second hollow bodies, respectively, and magnetically couple the first and second anastomotic components and form an anastomosis.

Yet another embodiment of the invention provides a method for coupling first and second magnetically attracted anastomotic components that are mounted on a delivery device and includes steps of providing at least first and second anastomotic components configured to be secured to a first hollow body, the first and second components being magnetically attracted to one another, providing a delivery device configured to support at least two anastomotic components, mounting the first anastomotic component on the delivery device, mounting the second anastomotic component on the delivery device, and using magnetic repulsion between a portion of the delivery device and the first anastomotic component to move it toward the second anastomotic component.

Another embodiment of the invention provides a delivery device for delivering at least one magnetic anastomotic component to form an anastomosis between first and second hollow bodies. The delivery device is configured to support an anastomotic component, and the anastomotic component includes at least two members magnetically attracted to one another. The two members of the anastomotic component are supported by the delivery device, and the delivery device includes an actuator that uses magnetic repulsion to move one of the members toward the other member.

BRIEF DESCRIPTION OF THE DRAWING FIGURES

FIGS. 7A through 7D are bottom plan views sequentially showing the delivery device being used to secure a first anastomotic component to a first vessel and then couple the first component to a second anastomotic component which is secured to a second vessel;

FIGS. 8A through 8D are side elevation views corresponding to FIGS. 7A-7D but showing a first vessel to which the first anastomotic component is being secured;

FIGS. 10A and 10B are perspective views of a delivery device constructed according to an alternative embodiment of the invention, wherein an anastomotic component is shown mounted on the delivery device prior to actuation of the device;

FIGS. 11A and 11B are, respectively, fragmentary side and end elevation views of the device and anastomotic component illustrated in FIGS. 10A and 10B;

DETAILED DESCRIPTION OF PREFERRED EMBODIMENTS

Figure 1A:
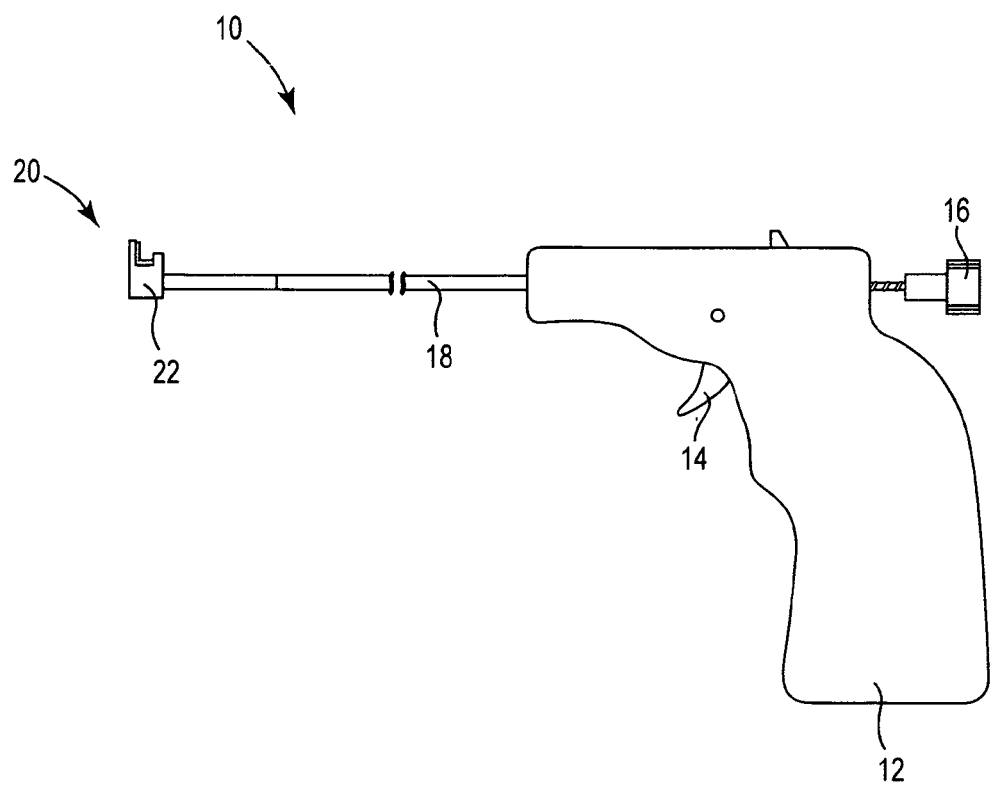
FIG. 1A is a side elevation view of a delivery device constructed according to one embodiment of the invention.
Figure 1B:
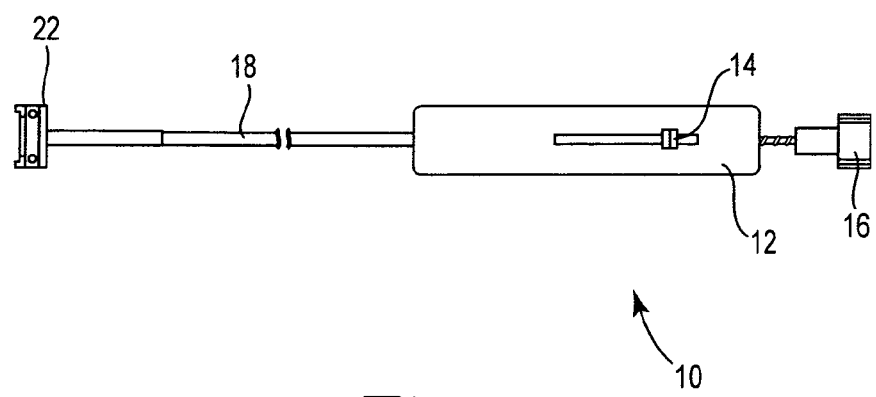
FIG. 1B is an upper plan view of the delivery device shown in FIG. 1A.

FIG. 1 shows an anastomotic delivery device 10 having a handle 12, first and second actuators 14, 16, and a shaft 18. The distal end of the delivery device 10 is indicated by the reference numeral 20 and is constructed to deploy a first anastomotic component that is configured to be coupled to a second anastomotic component, thereby forming a magnetic anastomosis. As used herein, the term anastomosis encompasses the connection of any two (or more) hollow anatomical structures, bodies, vessels, etc.

The distal end 20 of delivery device 10 is used to secure a first anastomotic component to a first vessel while supporting a second anastomotic component secured to a second vessel (the components and vessels not being shown in FIGS. 1A and 1B and 2A-2C). In the illustrated embodiment the distal end 20 includes a cradle 22, which is described in detail below with reference to FIGS. 3 and 4A-4C. The cradle 22 receives the second anastomotic component and a portion of the vessel to which it is attached. The delivery device 10 is used to secure the first anastomotic component to its vessel as well as magnetically couple the first and second anastomotic components to form the anastomosis.

Figure 2A:
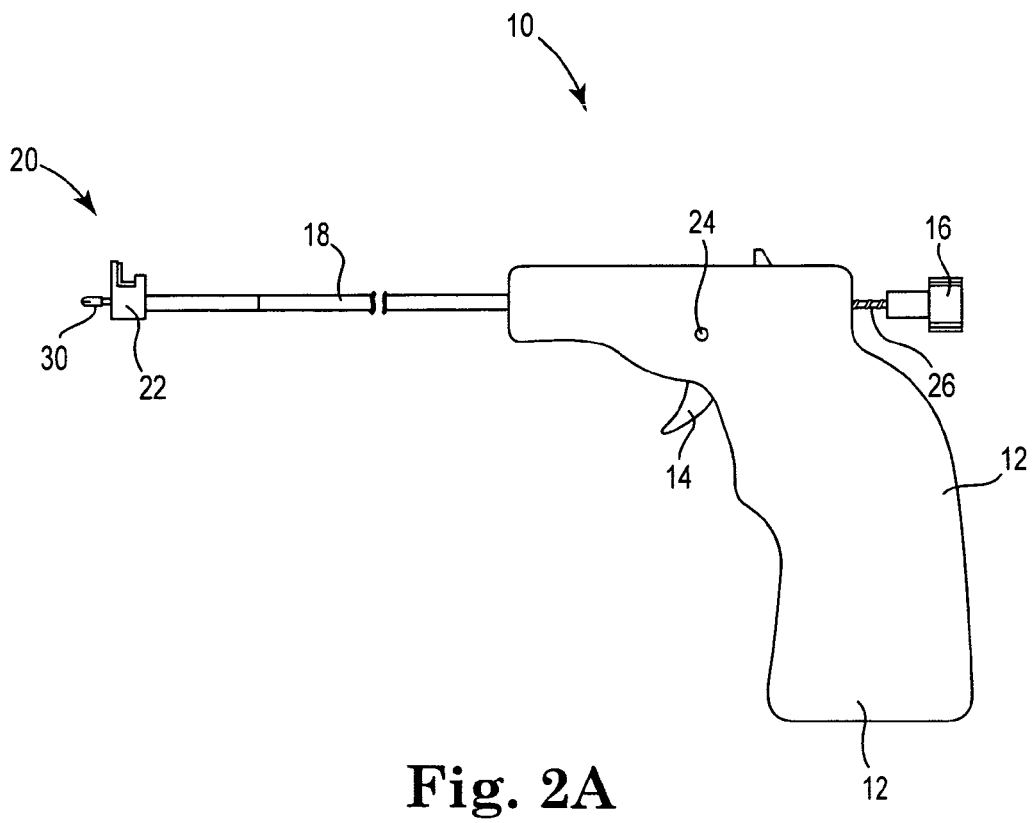
FIG. 2A is a side elevation view of the delivery device shown in FIG. 1A with the nose cone of the device in an extended position.
Figure 2B:
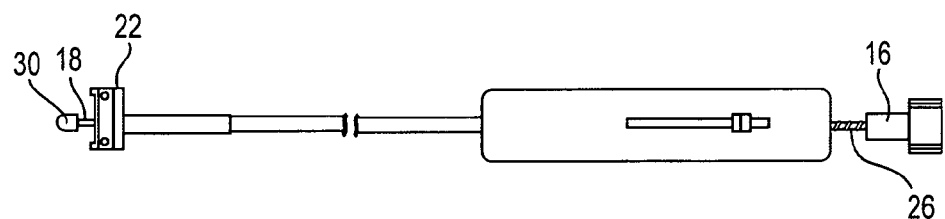
FIG. 2B is an upper plan view of the delivery device shown in FIG. 2A.
Figure 2C:
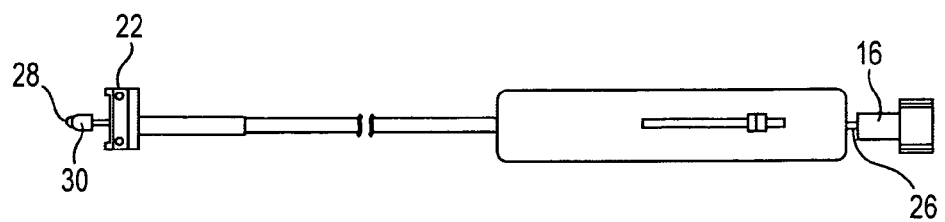
FIG. 2C is an upper plan view of the delivery device shown in FIGS. 2A and 2B with a cutting tip extending from the nose cone.

The delivery device 10 preferably is pistol-shaped as shown, but could take alternative configurations. The first actuator 14 preferably has a safety 24 and is operably coupled to the shaft to effect distal and proximal motion of the shaft (i.e., to the left and right in FIG. 1A, respectively). The second actuator 16 is used to operate a tissue penetrating mechanism which, in the illustrated embodiment, comprises a shaft 26 with a cutting tip 28 at its distal end. The shaft 26 is spring loaded so that pressing the second actuator 16 exposes the cutting tip 28 by moving it beyond a nose cone 30. FIGS. 2B and 2C show, respectively, the cutting tip 28 in a retracted position and an extended, tissue cutting position.

Figure 3:
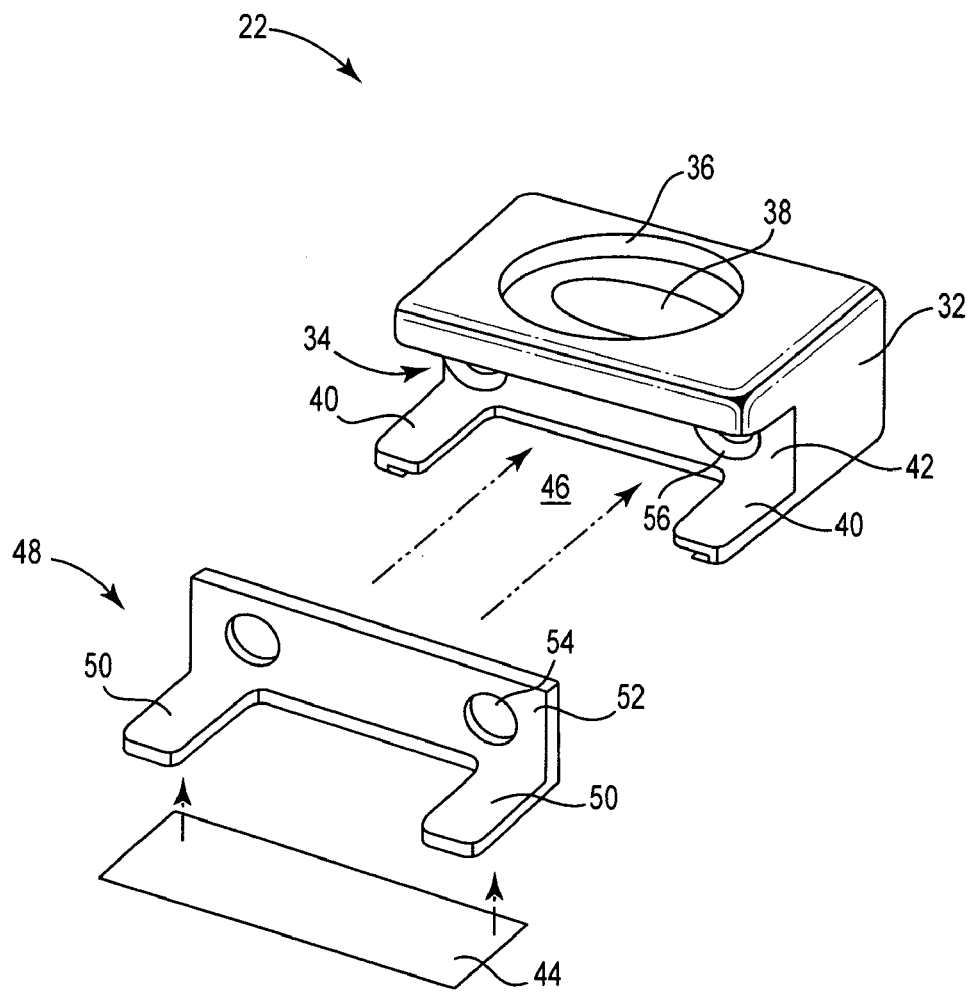
FIG. 3 is a perspective exploded view of a cradle disposed at the distal end of the delivery device.

FIG. 3 is an exploded view of the cradle 22 of the delivery device 10. The cradle 22 includes a base 32, which may be somewhat U-shaped so as to define a space 34 along its one side. The base 32 has a bore 36 to which shaft 18 is secured, as well as a bore 38 through which an inner shaft (not shown) extends. The inner shaft (FIG. 6A) is preferably provided with an exterior configured to be complimentary to an anastomotic component (not shown) mounted thereon. The base 32 includes two ledges 40 that, along with a wall 42, partially define the space 34. The ledges 40 support a transfer member 44 that is used to align and, according to the preferred embodiment, couple magnetic anastomotic components.

The transfer member 44 is preferably a thin sheet sized to rest on the ledges 40 of the base 32. When positioned on the base 32 the transfer member 44 overlies a gap 46 located between the ledges 40. While the transfer member 44 could be formed as part of the base, in the illustrated embodiment it is a separate element that is held in position by a clamp 48. The clamp 48 is generally L-shaped with a pair of horizontal legs 50 adapted to overlie the ledges 40 of the base 32. As shown, the legs 50 define a gap that overlies the gap 46 of the base 32 when the clamp 48 is attached thereto, which leaves the transfer member 44 uncovered in that area. The clamp 48 also has a vertical leg 52 adapted to be secured to the wall 42 of the base 32 by any suitable means, for example, mating apertures 54, 56 and fasteners (not shown).

Figure 4A:
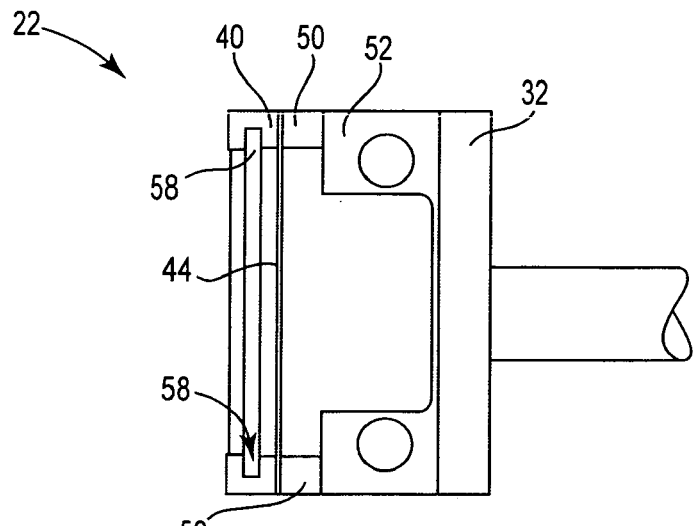
FIGS. 4A, 4B and 4C are, respectively, upper plan, side elevation, and end elevation assembly views of the cradle shown in FIG. 3.
Figure 4B:
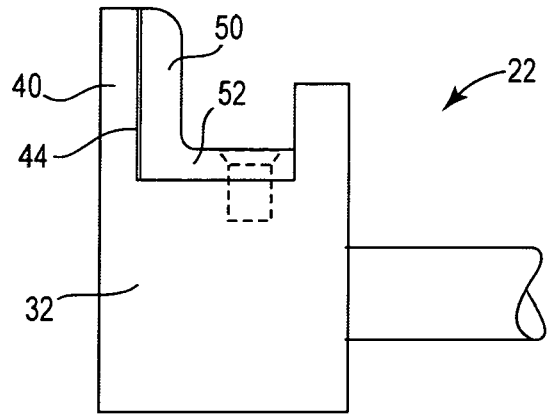
Figure 4C:
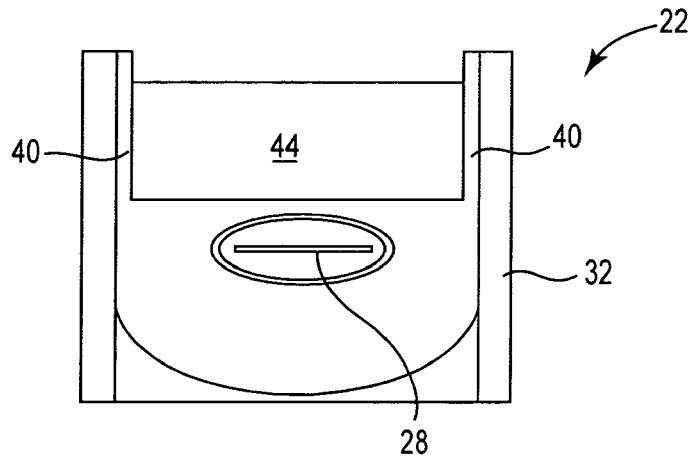

FIGS. 4A, 4B and 4C show the cradle 22 with the transfer member 44 and clamp 48 attached thereto. The base 32 is configured to support an anastomotic component (not shown in FIGS. 4A-4C) while it is being secured to a target vessel. The base 32 has slots 58 (FIGS. 3 and 4A) which receive an anastomotic component in removable fashion.

Figure 5:
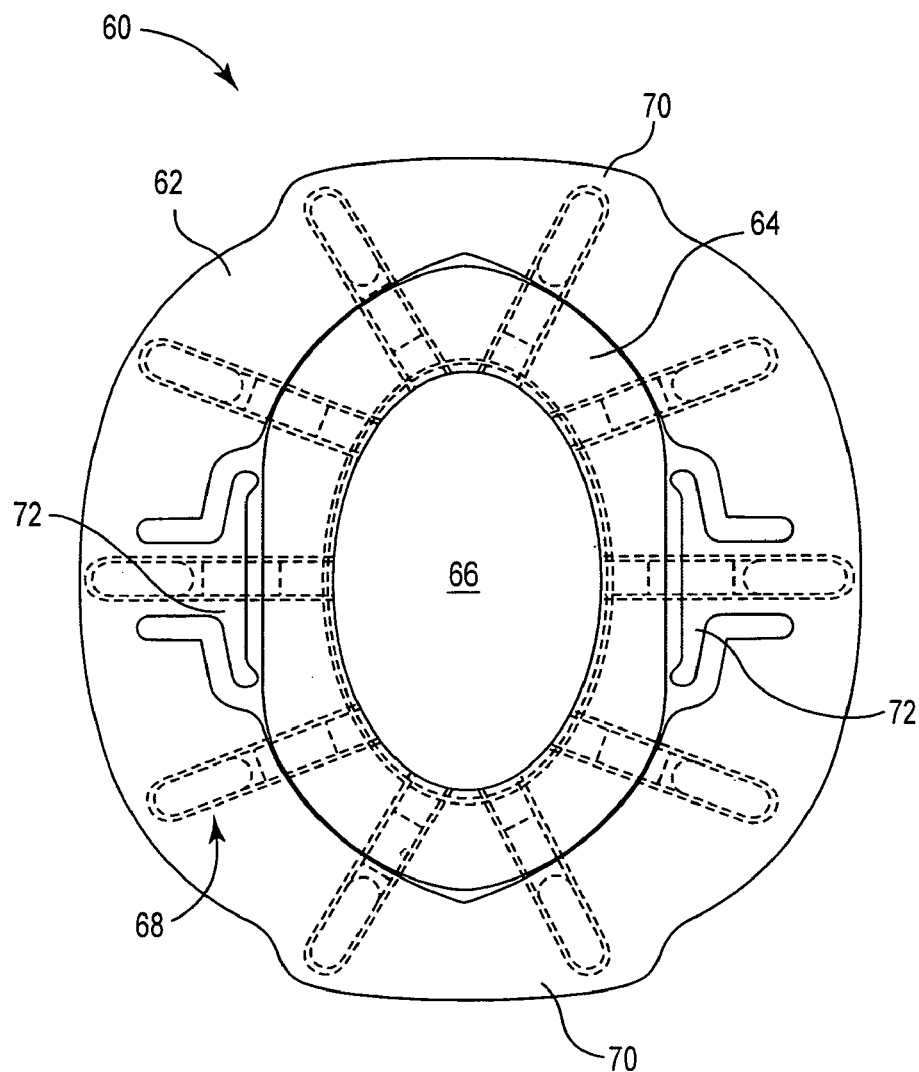
FIG. 5 is an upper plan view of a magnetic anastomotic component constructed according to one embodiment of the invention.

FIG. 5 shows one preferred anastomotic component constructed according to the invention and suitable for use in forming a magnetic anastomosis. The anastomotic component 60 includes an annular base 62, a magnet 64 with an opening 66 mounted on the base, and a vessel attaching mechanism 68. The base 62 also has tabs 70 sized to be slidably received in the slots 58 of the cradle 22. The tabs 70 are slid into the slots 58 until the opening 66 of the component 60 is aligned with the bores 36, 38 of the delivery device 10.

The magnet 64 may be attached to the base 62 of the anastomotic component 60 in any suitable manner, for example, adhesively, mechanical locking, etc. In the illustrated embodiment, the base 62 has locking tabs 72 for engaging and locking the magnet 64. It will be appreciated that the specific construction of the anastomotic component may be varied from that illustrated. It will also be recognized that the anastomotic component could be removably mounted on the delivery device in manners other than described herein.

An important feature of the illustrated anastomotic component 60 facilitates improved attachment to vessels. In particular, it is desirable in some cases to use a component with an elliptical profile. The anastomotic component 60 achieves equal spacing at the tips 76 of the members 74, which requires unequal spacing of the opposite ends of the members, as shown in FIG. 5. The equally spaced tips provide increased holding force and improved sealing, as compared to a plurality of arms that are unequally spaced at their tips. This is particularly true for attachment members or arms that rely on their distal tips, as opposed to their entire length, to engage tissue.

Figure 6A:
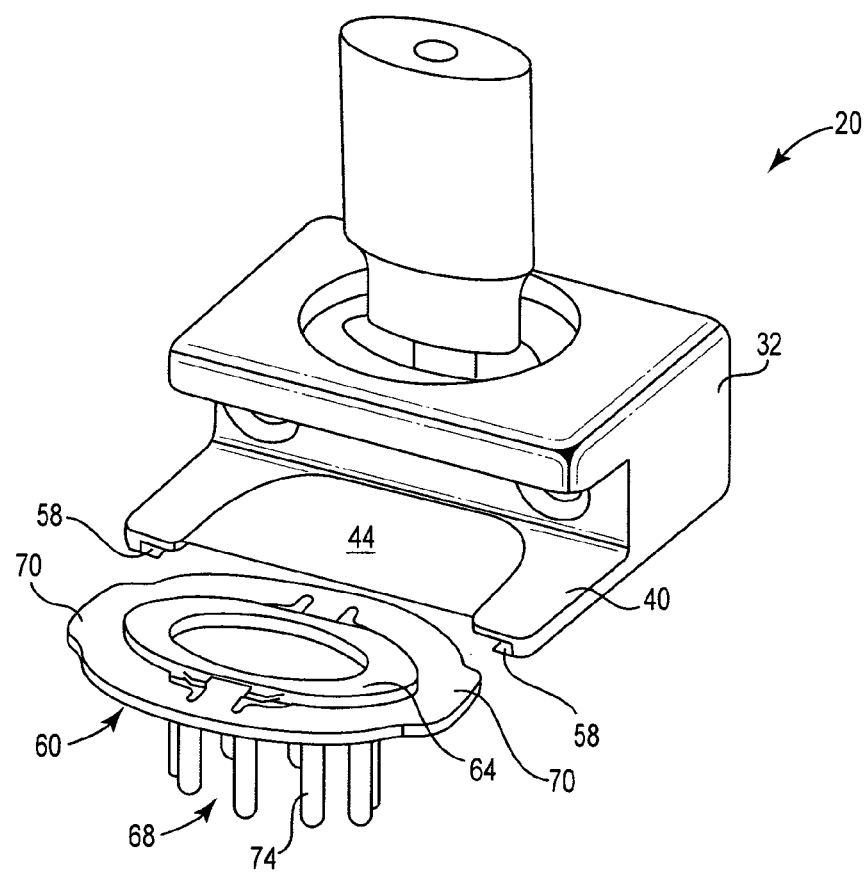
FIGS. 6A through 6G are sequential perspective views of the distal end of the delivery device being used to couple first and second anastomotic components to form an anastomosis between first and second vessels.

An exemplary application for the invention will be described with reference to FIGS. 6A through 6G, wherein the delivery device 10 is used to deploy a first anastomotic component and then magnetically couple it to a second anastomotic component thereto. FIG. 6A shows the above-described distal end 20 of delivery device 10 positioned alongside the above-described magnetic anastomotic component 60 (FIG. 5). The tabs 70 of the component 60 are positioned adjacent the slots 58 in the base 32 of cradle 22.

The vessel attaching mechanism 68 of the anastomotic component 60 is shown in FIG. 6A in a collapsed orientation for loading onto the delivery device 10. The illustrated mechanism 68 includes a plurality of tissue engaging members 74 which are designed to move to an expanded orientation in order secure the anastomotic component 60 to a target vessel (omitted for clarity).

Figure 6B:
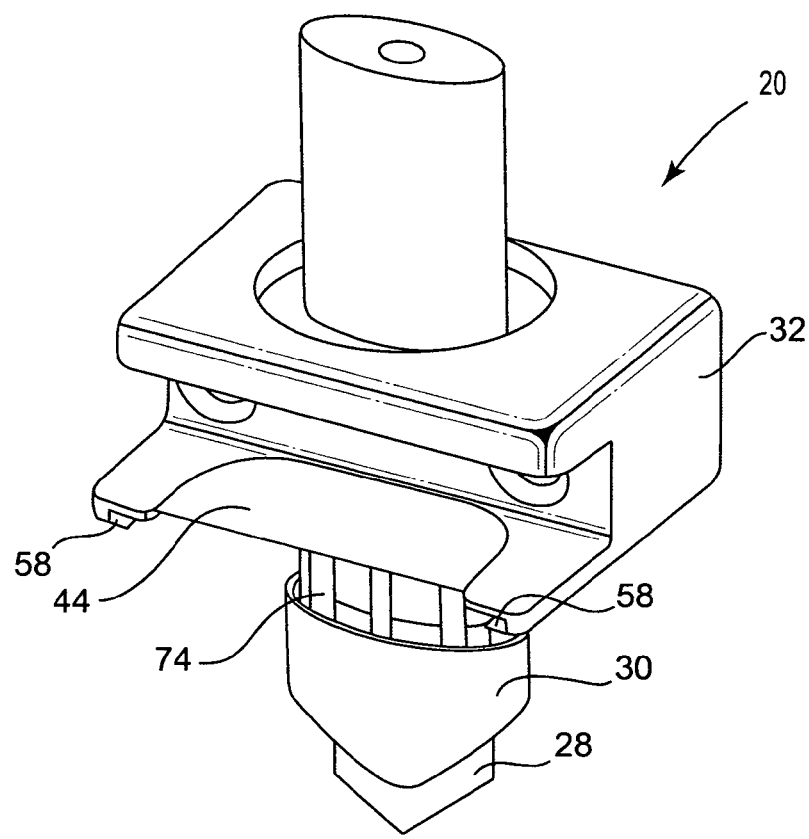

FIG. 6B shows anastomotic component 60 after the tabs 70 thereof have been fully inserted into slots 58, which aligns the opening 66 of magnet 64 with the shaft 18. The shaft 18 is moved distally until the nose cone 30 has cleared the tips 76 of the tissue engaging members 74, and then it is retracted to capture the tips 76 within a recess 78 formed in the nose cone 30. This holds the tissue engaging, mechanism 68 in its collapsed orientation with the members 74 radially retracted. The actuator 14 is preferably constructed so that a single motion causes the nose cone 30 to move distally and then proximally through the component.

Figure 6C:
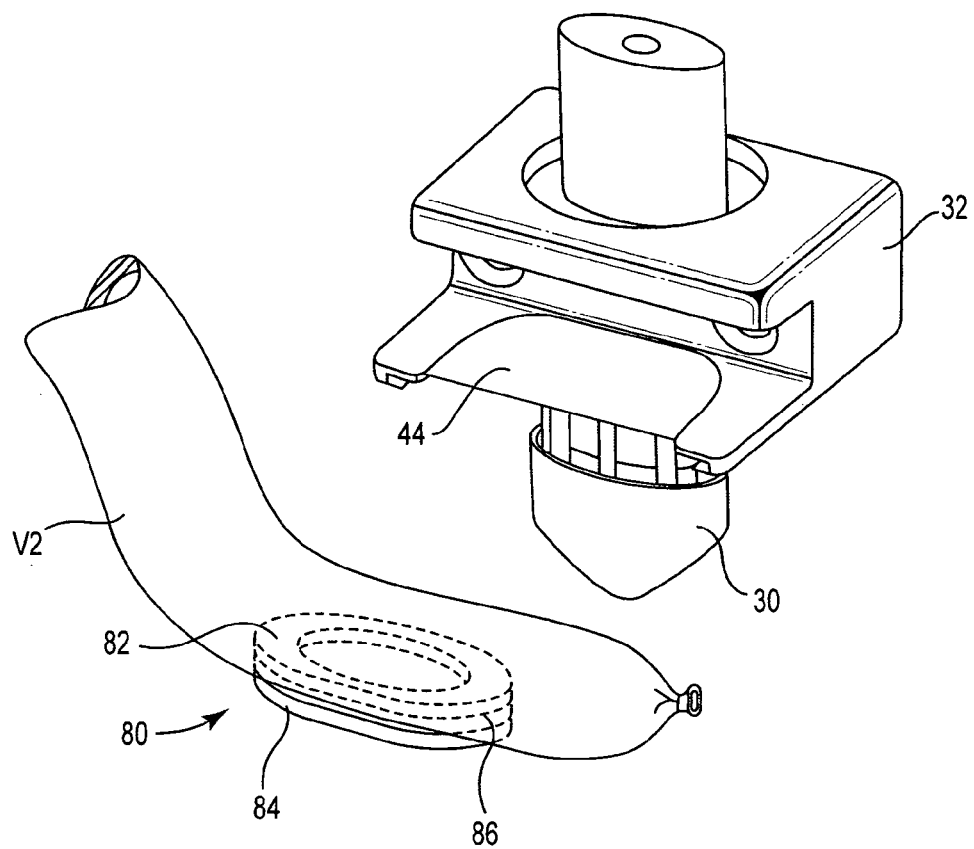

FIG. 6C shows a vessel V2 positioned adjacent the cradle 22 and the first anastomotic component 60 (which is in the same position illustrated in FIG. 6B). The vessel V2 has secured thereto a second anastomotic component 80 comprising magnetically attracted rings 82, 84. The rings 82, 84 are respectively positioned on the inner and outer surfaces of the vessel V2 so as to sandwich the vessel wall 86 therebetween. It should be noted that while the second anastomotic component 80 is shown secured to a side wall of the vessel V2, it could instead be secured to the end of the vessel V2, for example, by passing the vessel end through one ring, everting it around over that ring, and then positioning the other ring against the everted tissue, with magnetic attraction securing the rings to the vessel.

Figure 6D:
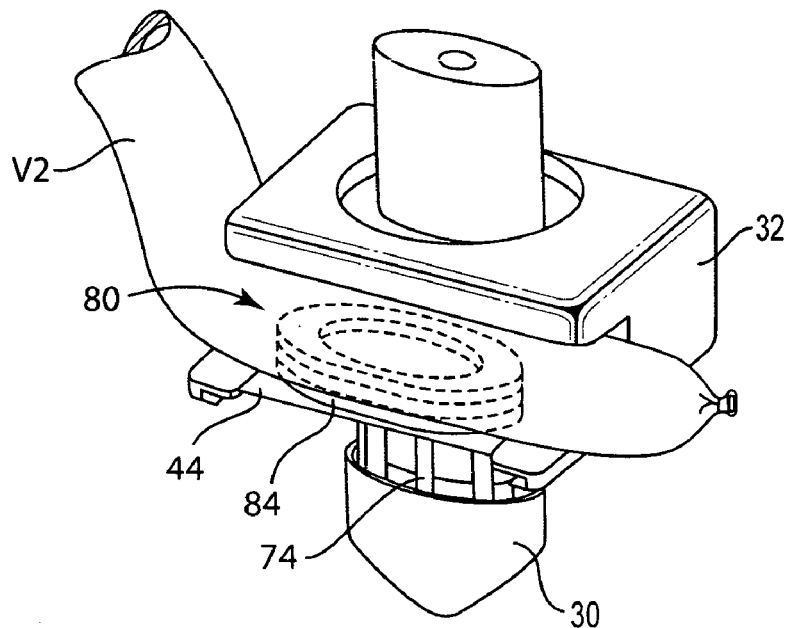

FIG. 6D shows the vessel V2 positioned in the space 34 defined by the cradle 22 with the second anastomotic component 80 located adjacent the transfer member 44. The outer ring 84 of component 80 is disposed on the transfer member 44 and sits between the ledges 40 of the base 32 (which define an elliptical area to receive the elliptical magnet ring). The transfer member 44 may be formed of various materials, but preferably is magnetic or ferromagnetic so that it is attracted to the magnetic anastomotic component. This magnetic attraction is used to properly orient the second anastomotic component 80 on the delivery device 10 and, according to another aspect of the invention, to move the component 80 into alignment with the first anastomotic component.

Figure 6E:
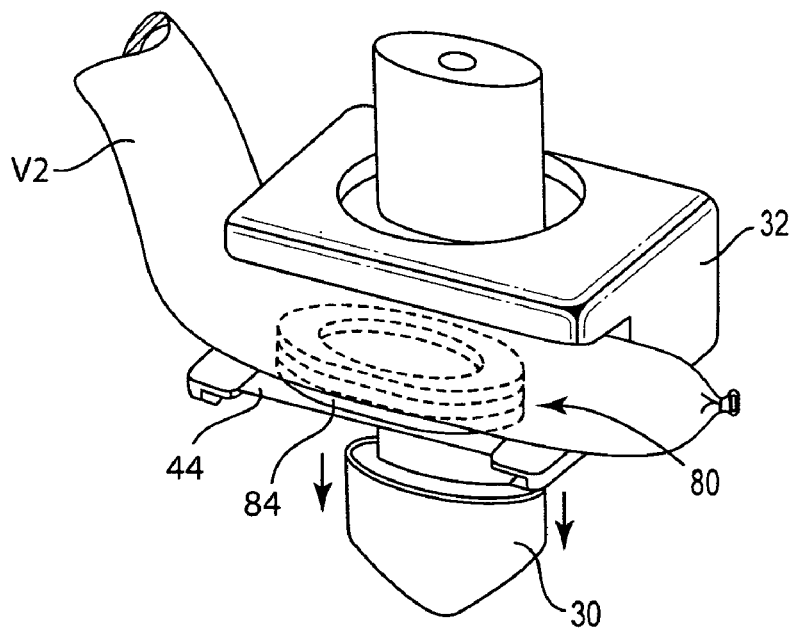
Figure 6F:
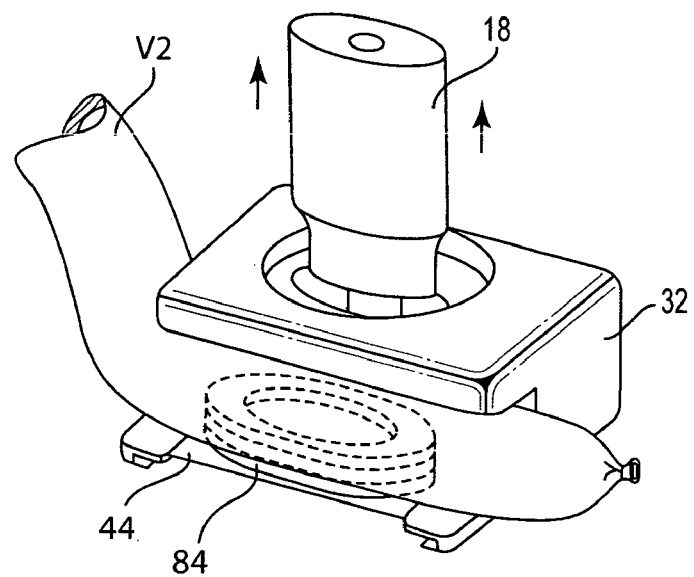

FIG. 6E shows the device 10 after the nose cone 30 has been moved distally to release the tissue engaging members 74 of mechanism 68, as indicated by the arrows. The nose cone 30 is then moved proximally through the opening 66 of the magnet 64, as shown in FIG. 6F. Next, the cradle 22 is moved in the direction of the arrows, which moves the transfer member 44 (and the second anastomotic component 80 held thereby) toward the first anastomotic component 60. It should be noted that the cradle, rather than being square or rectangular, could be round so as to allow movement in multiple directions with respect to the anastomotic components.

Figure 6G:
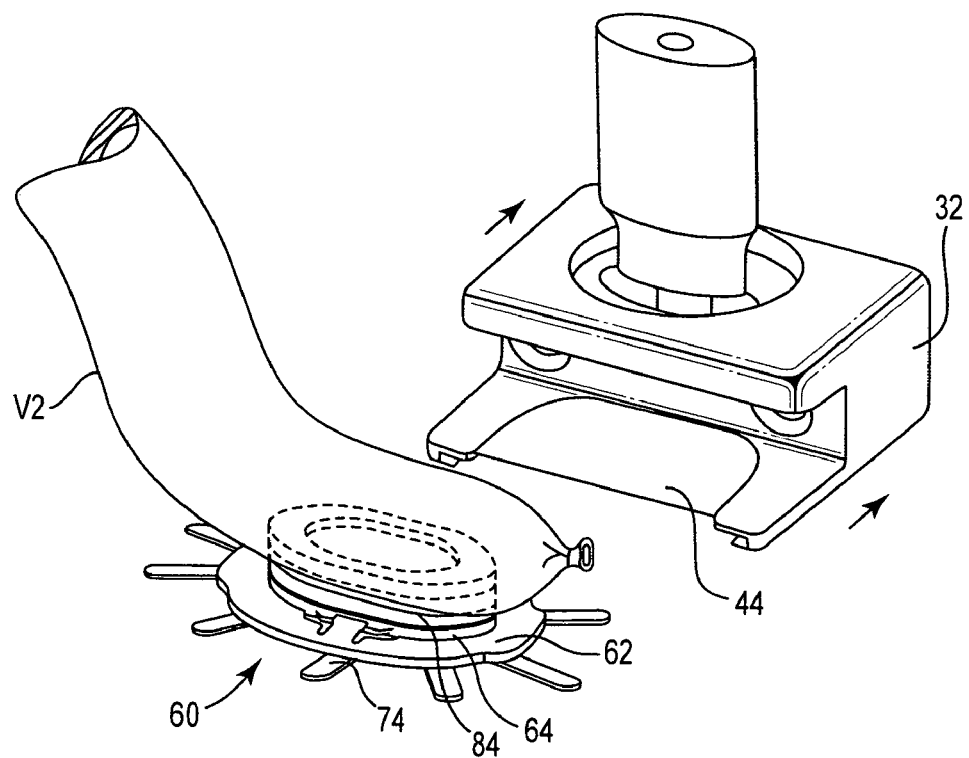

Once the second anastomotic component 80 has been moved by the transfer member and is aligned with the first anastomotic component 60, the transfer member 44 is moved further in the direction of the arrows. This motion slides the transfer member 44 from in between the two components, which allows the components to become magnetically coupled. More specifically, although the second anastomotic component 80 is magnetically held against the transfer member 44, its attraction to the first component 60 is much stronger. As a result, the transfer member 44 releases the second anastomotic component 80, which leaves the components 60, 80 in face-to-face contact, as shown in FIG. 6G. FIG. 6G shows the tissue engaging members 74 in their expanded position, in which they cooperate with the component base 62 to compress the target vessel tissue (omitted for clarity) and secure the first anastomotic component 60 thereto.

FIGS. 7A-7D are bottom plan views sequentially illustrating the members 74 of the first anastomotic component 60 being expanded, the transfer member 44 being used to move the outer ring 84 of the second anastomotic component 80 into alignment with the magnet 64 of the component 60, and the transfer member 44 being slid from between the two anastomotic components. When the tabs 70 clear the slots 58 the transfer member 44 should be moved from beneath the component 80, which ensures that the delivery device 10 will not be pulled away and lift the component 80 from the component 60.

FIGS. 8A-8D are sectional views corresponding to FIGS. 7A-7D, but showing a first vessel V1 to which the first anastomotic component 60 is being secured. (The second vessel V2 is omitted from these views for clarity.) FIGS. 8C and 8D illustrate another aspect of the invention wherein the opening extending into the vessel V defined by the anastomotic component 60 is sealed during alignment of the components.

FIG. 8C shows the transfer member 44 partially over the opening 66 of component 60 (with the shaft and nose cone over the rest of the opening). In this position, blood is blocked by the transfer member 44, although some blood may enter the bore that receives shaft 18. The blood could be blocked instead, or a flashback lumen could be provided if desired. FIG. 8D shows the transfer member 44 after it has been further moved to align the first and second anastomotic components 60, 80. In this position, the transfer member 44 is disposed between the components 60, 80 and blocks blood flow out of the vessel V2. From the position of FIG. 8D the transfer member 44 is slid out to couple the components 60, 80.

Figure 9A:
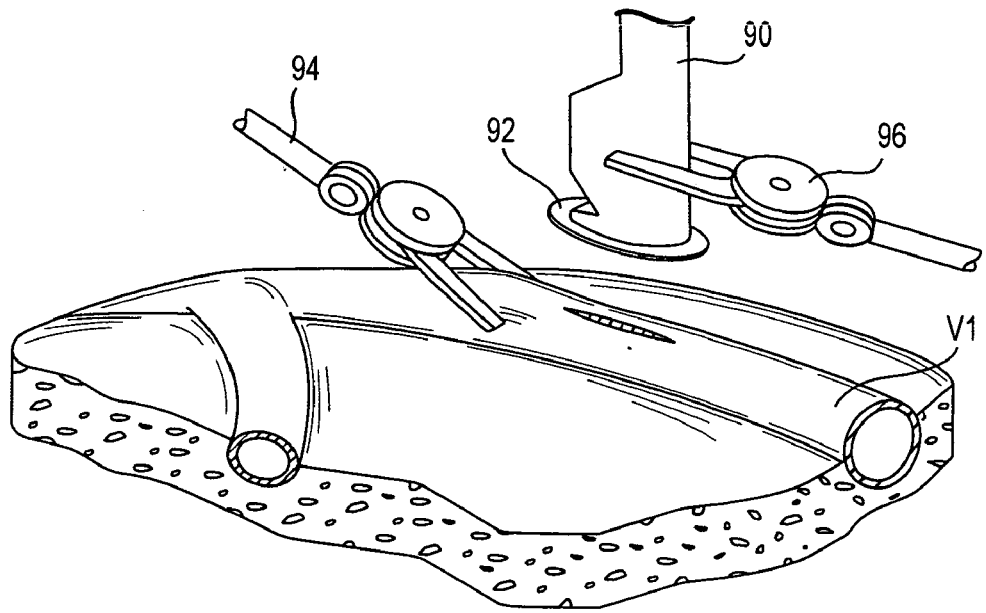
FIGS. 9A through 9F are perspective views sequentially showing the use of a robotic system to form a magnetic anastomosis according to another embodiment of the invention.

According to another embodiment of the invention, a robotic system is used to form a magnetic anastomosis. Referring to FIGS. 9A-9F, a delivery device 90 is schematically shown and has mounted thereon an anastomotic component 92. A pair of robotic elements 94, 96 is provided with one or more jaw or pincer mechanisms. FIG. 9A shows robotic element 94 stabilizing a target vessel V1 (for example, a coronary artery) while the element 96 holds the delivery device 90.

Figure 9B:
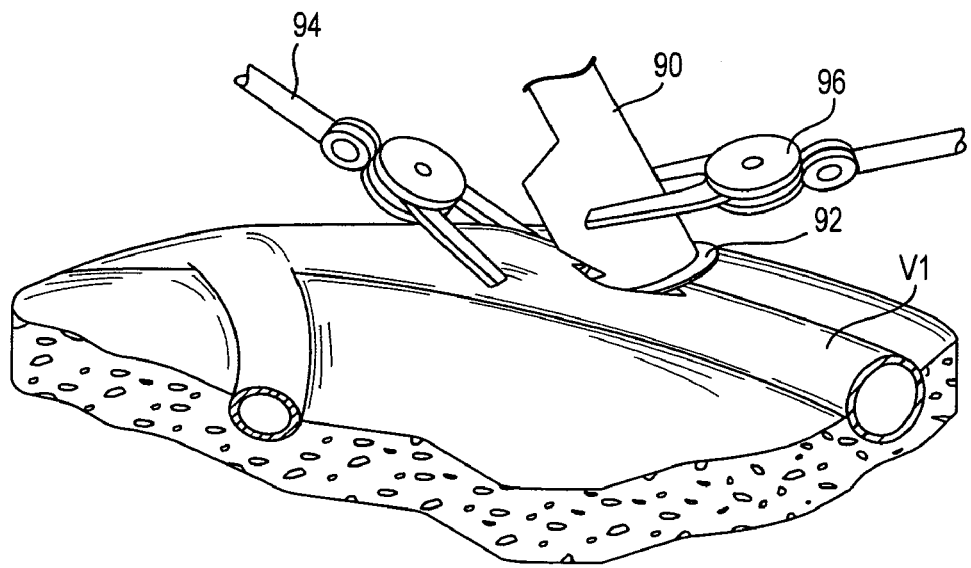
Figure 9C:
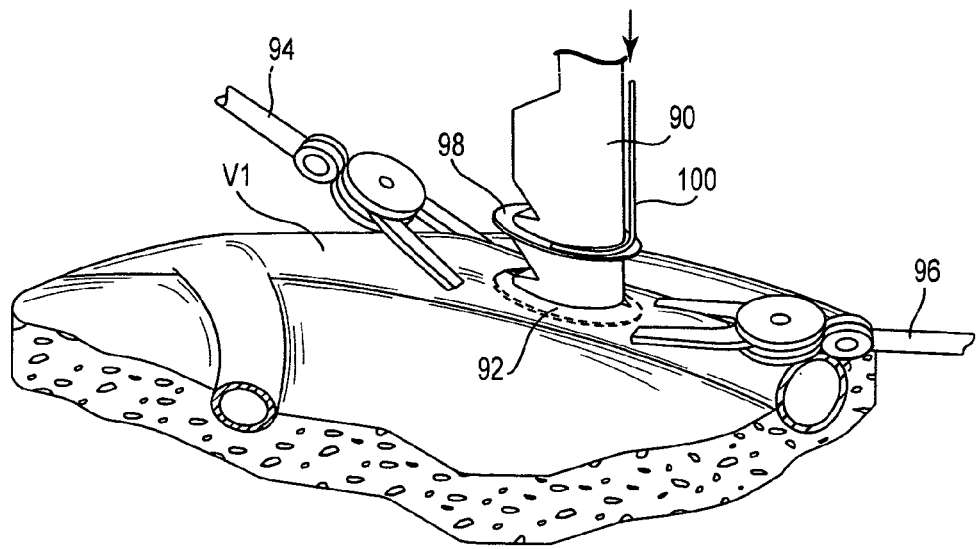

As shown, an incision or other opening has been formed in the vessel wall, either by robotics or manually. The opening is sized to receive the distal end of the delivery device 90 and the anastomotic component 92, as shown in FIG. 9B. (The robotic element holding the delivery device is omitted from FIGS. 9C and 9D for clarity.) FIG. 9C shows the anastomotic component 92 located in the lumen of the vessel V1 while another anastomotic component 98 is moved toward the vessel wall. An actuator 100 moves the anastomotic component 98 toward the component 92 until magnetic attraction causes the two components to sandwich the wall of vessel V1. The actuator 100 may be moved manually or by one of the robotic elements.

Figure 9D:
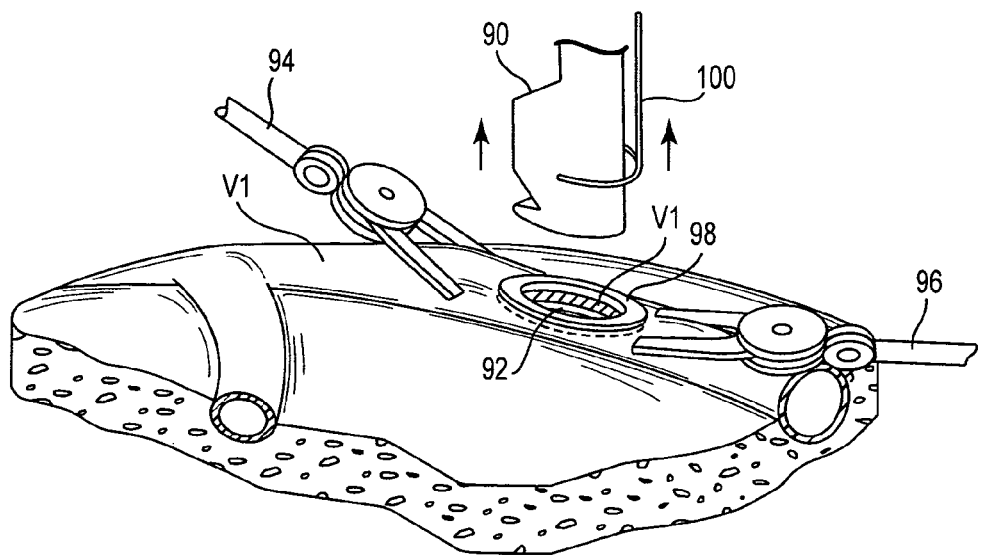

FIG. 9D shows the delivery device 90 being subsequently removed and the resulting port that is formed in the vessel V1. The delivery device 90 is provided with a mechanism (not shown) that it actuated to release the anastomotic components once they have been secured to the vessel and coupled to place the vessels in fluid communication. The delivery device 90 may have a component release mechanism constructed according to the teachings of abovementioned application Ser. No. 09/638,805, the subject matter of which has been incorporated by reference herein.

Figure 9E:
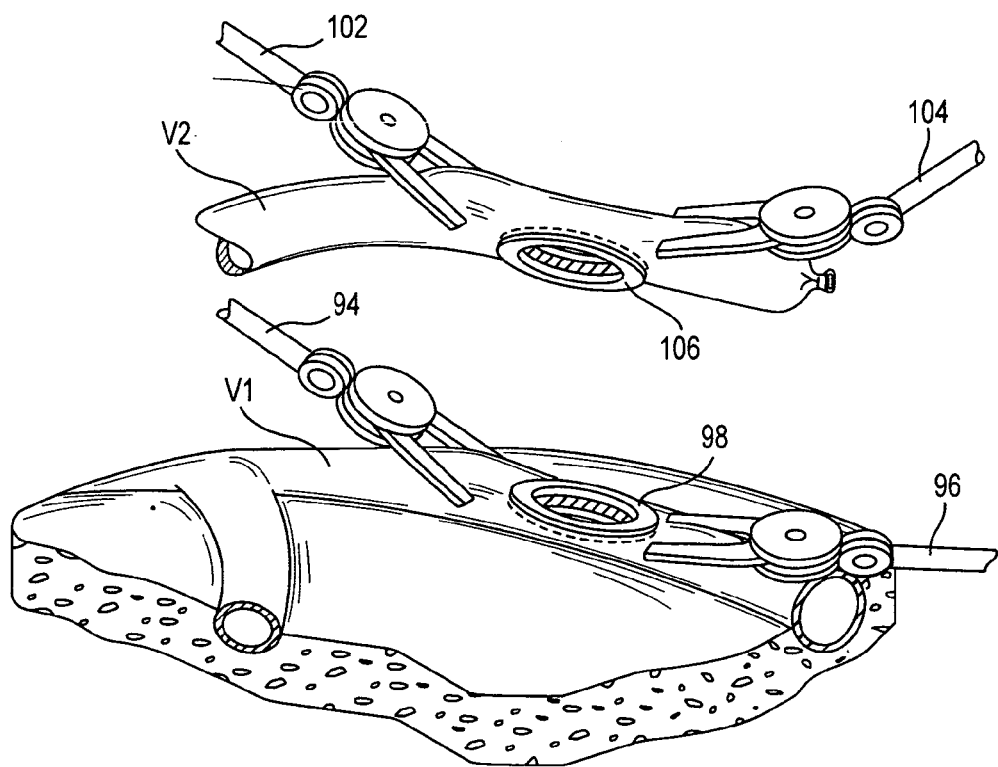
Figure 9F:
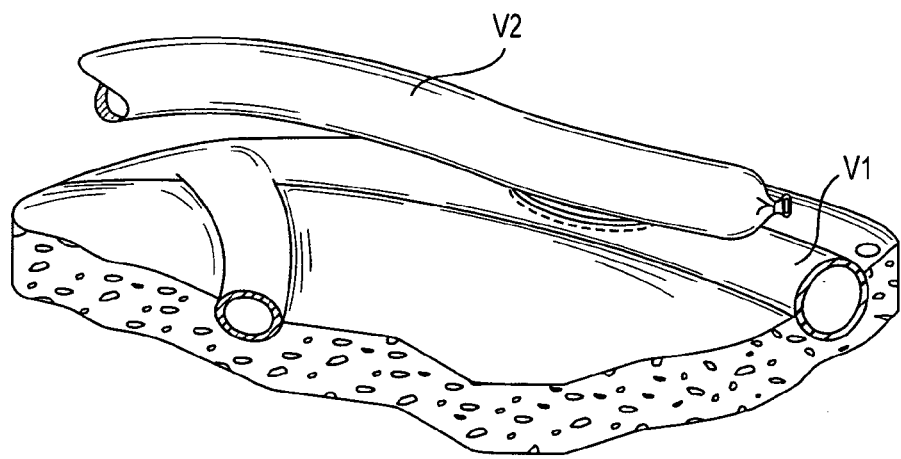

FIG. 9E shows another pair of robotic elements 102, 104 being used to approximate a second vessel V2 with the first vessel V1, the latter having a magnetic port formed by an anastomotic component 106. Approximating the vessels V1, V2 brings the anastomotic components 98, 106 toward each other until they are coupled by magnetic attraction to form the anastomosis, as shown in FIG. 9F.

It should be recognized that practicing this embodiment of the invention does not require the use of a specialized robotic system. To the contrary, any suitable robotic system may be used, for example, one of the known computerized surgical systems for performing various medical procedures. Those skilled in the art will nonetheless appreciate that in some applications it may be desirable or necessary to adapt an available robotic system for use with the delivery devices and anastomotic components of the present invention.

For example, in the embodiment of FIGS. 9A through 9F, the delivery device 90 is held by the end effector (pincer jaws) of the robotic element 96. Alternatively, the delivery device of the invention may be formed as an integral part of the robotic element, for example, the end effector of the robotic element may be in the form of an anastomotic delivery device. The robotic elements may include, in addition to a delivery device, pincer jaws, graspers or other known structure for holding, manipulating and actuating the delivery device. Finally, rather than forming a portion of the robotic element as the delivery device, one or more selected features of an inventive delivery device could be included in an otherwise conventional robotic element.

It should also be recognized that the number and type of functions performed by the robotic elements may vary from procedure to procedure. In the embodiment of FIGS. 9A though 9F, the robotic elements are first used to position and actuate the delivery device to secure each anastomotic component to its vessel. Next, the robotic elements are used to grasp and approximate the vessels and couple the components to complete the anastomosis.

The anastomosis could alternatively be carried out without using the robotic system to perform each step of the procedure. For example, the robotic elements may be used to hold and position, but not actuate, the delivery devices. As an example, a minimally invasive procedure may be carried out using several robotic elements inserted through small ports in the patient to hold the delivery devices in the desired position. The surgeon could then actuate a delivery device without using robotics, for instance, by passing pass the shaft of a remotely-operated instrument (such as a cable-actuated device of the type used in laparoscopic surgery) through a port to a position adjacent the delivery device. The surgeon could then operate the instrument from outside the patient's body to actuate the delivery device and deploy the anastomotic components.

As noted above, it should be appreciated that the delivery device illustrated in FIGS. 9A through 9F is an exemplary embodiment and represents only one possible means for practicing the invention. FIGS. 10A through 13B show a delivery device, designated by reference numeral 110, which is constructed according to another embodiment of the invention. The delivery device 110 is configured to be used in a robotic procedure and has a small profile to permit use in a minimally invasive procedure. The relatively small size of the delivery device 110 permits it to be introduced into a patient's body through a small incision or port unlike devices designed for use in more open surgical procedures. Although the delivery device 110 is constructed to be held by a robotic element such as that shown in FIGS. 9A through 9F, it may also be used with a manually operated surgical instrument.

Referring to FIGS. 10A and 10B, the delivery device 110 comprises a body 112 having upper and lower portions 114, 116 configured to support, respectively, first and second anastomotic components 118, 120. The delivery device 110 has an actuator 122 which deploys and then releases the components 118, 120. The upper portion 114 of the delivery device 110 is provided with a retainer 124 that holds the anastomotic component 118 until the component 120 has been properly positioned with respect to the opening in the vessel. Next, the actuator 122 is used to release the first component 118 from the retainer 124 and allow it to be coupled to the second component 120. The second component 120 is held on the delivery device 110 by a retainer 126 located on the lower portion 116 of the body 112. Further actuation of the actuator 122 releases the second component 120 (as well as the first component 118 coupled thereto) from the retainer 126 to remove the delivery device.

FIGS. 10A, 10B, 11A and 11B show the delivery device 110 prior to actuation with the anastomotic components 118, 120 being held in place by the retainers 124, 126, respectively. The body 112 has a bore 128 in which a plunger 130 is slidably received, the plunger having the retainer 126 at its distal end. A spring 132 biases the plunger in a proximal direction which forces a pair of tabs 134 of retainer 124 away from the upper portion 114 of the device body 112. In this position the tabs 134 contact the lower surface of the first anastomotic component 118 and hold it away from the second component 120.

The actuator 122 is depressed to move the plunger 130 distally, which causes the tabs 134 to retract into the body 112 of the delivery device 110. As a result, the first anastomotic component 118 is no longer retained as it is in FIGS. 11A and 11B, but rather is free to be moved to a coupling position. In a preferred embodiment the delivery device utilizes magnetic repulsion to couple the anastomotic components.

The illustrated delivery device 110 includes an annular magnet 135 mounted on the upper portion 114 of the device body 112 adjacent the first anastomotic component 118. The magnet 135 is preferably a permanent magnet that is oriented on the device body to have the same polarity as the adjacent anastomotic component 118. Consequently, once the tabs 134 of retainer 124 are retracted into the device body 212, the first anastomotic component 118 is repelled by magnet 135 toward the outer surface of the vessel wall.

Figure 12A:
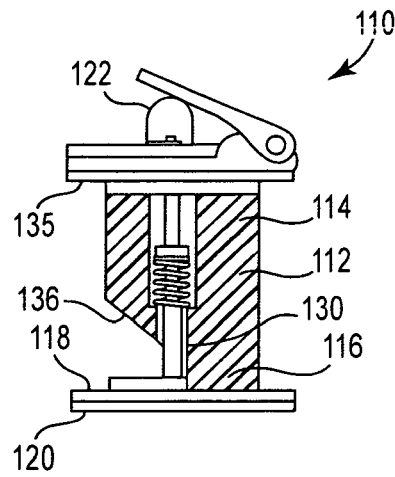
FIGS. 12A and 12B are, respectively, fragmentary side and end elevation views of the device and anastomotic component illustrated in FIGS. 11A and 11B after partial actuation of the device.
Figure 12B:
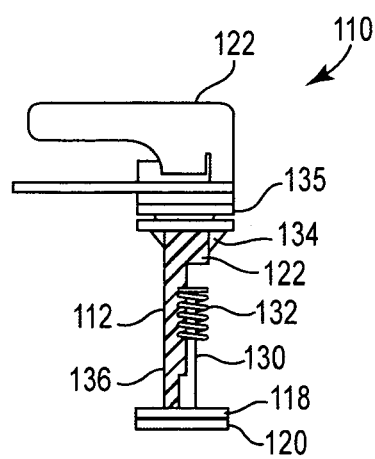
Figure 13A:
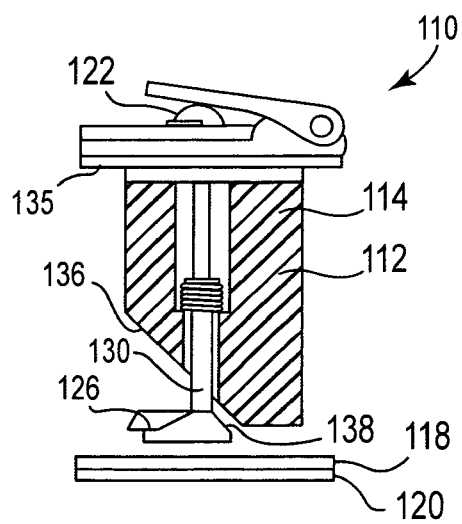
FIGS. 13A and 13B are, respectively, fragmentary side and end elevation views of the device and anastomotic component illustrated in FIGS. 12A and 12B after further actuation of the device.
Figure 13B:
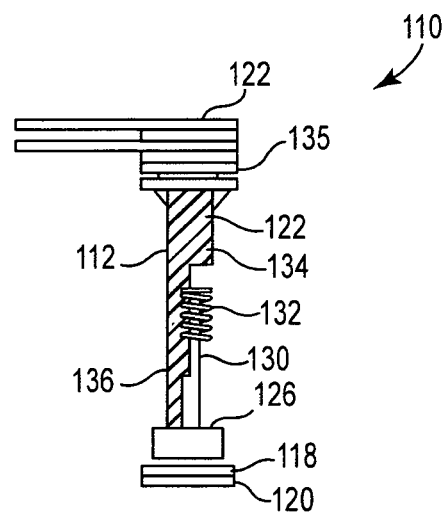

FIGS. 12A and 12B show the delivery device 110 after the actuator 122 has been partially actuated to retract the tabs 134 and the anastomotic component 118 has been repelled by the magnet 135. FIGS. 13A and 13B show the delivery device 110 after the actuator 122 has been further actuated to release the first and second anastomotic components 118, 120 from the retainer 126 and allow the delivery device to be removed.

As shown best in FIG. 13A, the body 112 of the delivery device 110 has a sloped surface 136, while the retainer 126 has a similarly shaped surface 138. Moving the plunger 130 distally moves the retainer 126 distally from the position shown in FIGS. 12A and 12B. This slides the ramped surface 138 of the retainer 126 along the sloped surface 136 of the device body 112, which moves the retainer 126 laterally toward the center of the device 110 (to the right in FIG. 11A) and out of engagement with the component 120 as well as the component 118.

Figure 14A:
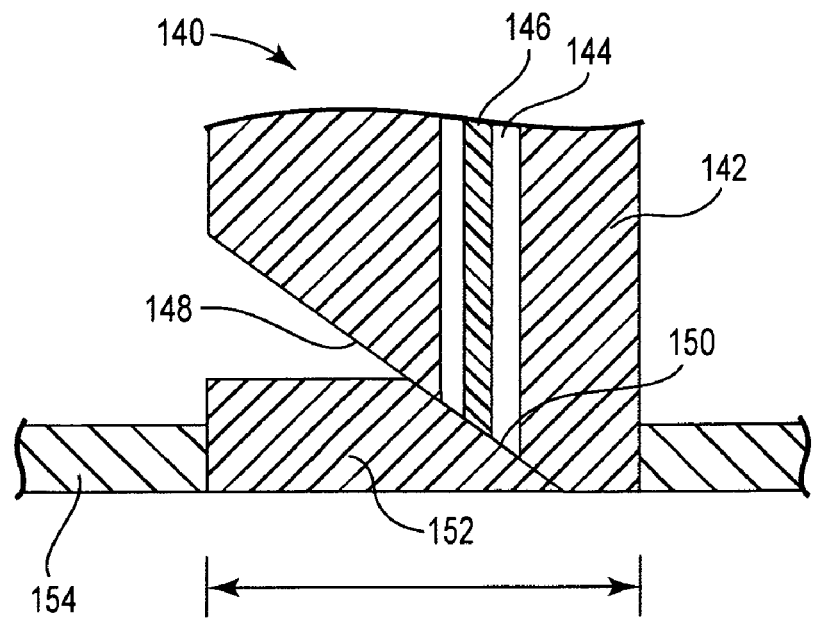
FIGS. 14A and 14B are side elevation views in section showing an exemplary actuator for the delivery device shown in FIG. 10A through FIG. 13B.
Figure 14B:
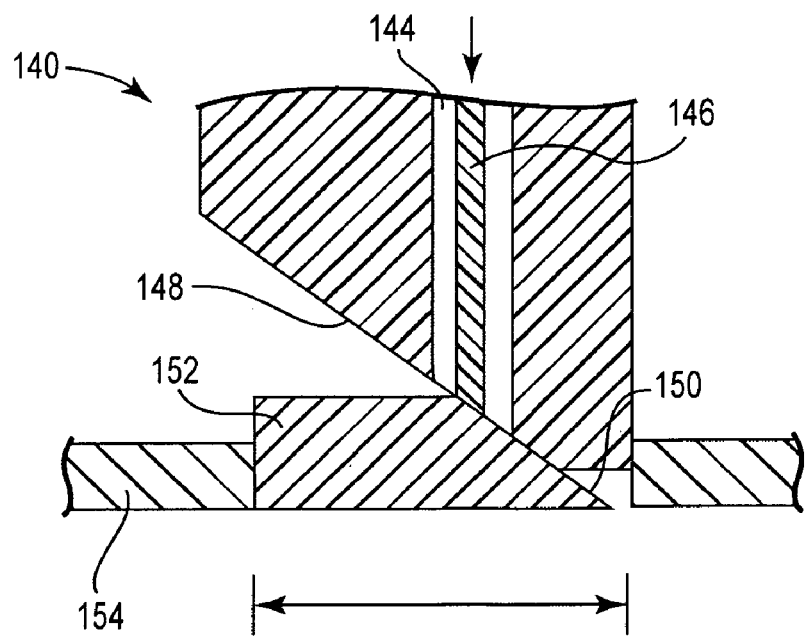

FIGS. 14A and 14B illustrate in schematic fashion the principle behind one possible means for releasing the anastomotic components from the delivery device according to the invention. A delivery device 140 has a body 142 provided with a bore 144 which slidably receives a plunger or shaft 146. The distal end of the device body 142 has a ramped surface 148 configured to slide along a ramped surface 150 formed on a retainer 152 carried by the plunger 146. FIG. 14A shows a magnetic anastomotic component 154 mounted on the distal end of the delivery device body 142 with the retainer 152 in its engaged position. As indicated by the arrow, the retainer 152 and the distal end of the delivery device body 142 combine to securely engage the inner diameter of the anastomotic component 154.

Actuation of the delivery device 140 moves the plunger 146 and retainer 152 distally from the position of FIG. 14A to the position of FIG. 14B. This slides the ramped surface 150 on the retainer 152 along the ramped surface 148 on the body 142 of the delivery device 140. Sliding the ramped surface 150 along the surface 148 moves the retainer 152 laterally (to the right in FIGS. 14A and 14B) and decreases its profile as indicated by the arrow. This disengages the retainer 152 from the inner diameter of the anastomotic component 154. It should be appreciated that the ramped surfaces shown in the illustrated embodiment represent only one possible way to transmit motion from an actuator to the working end of the delivery device in order to form an anastomosis according to the invention The magnetically attracted anastomotic components of the invention are adapted to be placed on opposite surfaces of a vessel wall and to sandwich the wall due to magnetic force. In some applications it may be desirable to provide one or more of the anastomotic components with additional or different vessel securing means; for example, the component may be attached to the vessel mechanically (e.g. by suturing) instead of or in addition to magnetically. The suture could be passed around the body of the anastomotic component and through the vessel wall, or the component could be provided with one or more suture anchors, for example, at spaced locations around its perimeter. The specific number, size, and location of suture anchors on the anastomotic component may of course vary depending on the application and user preference.

Other features, aspects and advantages of the invention beyond those specifically discussed will be apparent to those skilled in the art. Many modifications, alterations and variations of the illustrated embodiments may be made without departing from the scope and spirit of the invention as defined by the claims.

What is claimed is:

1. A method for forming an anastomosis between first and second hollow bodies using magnetic force, the method comprising steps of: receiving first and second anastomotic components respectively configured to be secured to first and second hollow bodies, the first and second components being magnetically attracted to one another; mounting the first component on a delivery device; securing the second anastomotic component to the second hollow body; mounting the second anastomotic component on the delivery device with the second hollow body secured to the second component; securing the first anastomotic component to the first hollow body; and using magnetism to couple the first and second anastomotic components and form an anastomosis between the first and second hollow bodies.

2. The method of claim 1, wherein the first and second hollow bodies are blood vessels.

3. The method of claim 2, wherein the first component is mounted on the delivery device in a collapsed configuration.

4. The method of claim 2, wherein the second anastomotic component is magnetically mounted on the delivery device.

5. The method of claim 4, wherein the second anastomotic component is mounted on a ferromagnetic sheet supported by the delivery device.

6. The method of claim 5, wherein the ferromagnetic sheet is manipulated to move the second anastomotic component into alignment with the first anastomotic component.

7. The method of claim 2, further comprising forming an opening in the first blood vessel prior to securing the first anastomotic component thereto.

8. The method of claim 7, wherein the opening is formed by an incising element carried by the delivery device.

9. The method of claim 2, wherein the delivery device has a cradle and a portion of the second hollow body is received in and supported by the cradle.

10. The method of claim 2, wherein the first anastomotic component has tabs received in slots formed in the delivery device.

11. The method of claim 2, wherein the first and second anastomotic components are coupled to form a side-to-side anastomosis between the first and second blood vessels.

12. A method for coupling first and second magnetically attracted anastomotic components mounted on a delivery device, the method comprising steps of: receiving first and second anastomotic components respectively configured to be secured to first and second hollow bodies, the first and second components being magnetically attracted to one another; providing a delivery device configured to support the first and second anastomotic components; mounting the first anastomotic component on the delivery device; mounting the second anastomotic component on the delivery device in a first position; moving the second anastomotic component from the first position to a second position; and using magnetism to couple the first and second anastomotic components.

13. The method of claim 12, wherein the delivery device has a transfer member holding the second anastomotic component, and the moving step is performed by moving the transfer member and second anastomotic component from the first position toward the first anastomotic component.

14. The method of claim 13, wherein the transfer member is moved until the first and second anastomotic components are aligned, and then is moved further to release the second anastomotic component from the delivery device.

15. The method of claim 14, wherein moving the transfer member further also releases the first anastomotic component from the delivery device.

16. The method of claim 14, wherein moving the transfer member allows the first and second anastomotic components to magnetically engage each other.

17. The method of claim 16, wherein the transfer member is moved to align and release the first and second anastomotic components.

18. The method of claim 13, wherein the second anastomotic component is magnetically attracted to the transfer member and is held in the first position by magnetic force.

19. The method of claim 18, wherein the transfer member is a sheet having ferromagnetic properties and the second anastomotic component comprises a permanent magnet attracted to the sheet.

20. A method for bypassing a portion of a blood vessel using magnetism, the method comprising steps of: receiving first and second anastomotic components that are magnetically attracted, respectively, to third and fourth anastomotic components; providing a graft vessel having a proximal portion adapted to be secured to a source of blood and a distal portion adapted to be secured to a target vessel so as to bypass a portion of the target vessel; securing the first anastomotic component to the proximal portion of the graft vessel and securing the second anastomotic component to the distal portion of the graft vessel; securing the third anastomotic component to a source of blood and securing the fourth anastomotic component to the target vessel at a location distal to the portion to be bypassed; using magnetism to couple the first and third anastomotic components together and form a proximal anastomosis; and using magnetism to couple the second and fourth anastomotic components together to form a distal anastomosis, wherein the distal anastomosis is formed before the proximal anastomosis.

21. The method of claim 20, wherein the blood source is the aorta and the target vessel is a coronary artery.

22. The method of claim 21, wherein the first and third anastomotic components are coupled without entering the lumen of the graft vessel.

23. The method of claim 21, wherein the third anastomotic component is secured to the aorta by a mechanical attachment.

24. The method of claim 21, wherein the graft vessel is an autologous blood vessel.

25. A method for forming an anastomosis between first and second hollow bodies using magnetic force, the method comprising steps of: positioning a first anastomotic component on a delivery device, the first anastomotic component adapted to be secured to a first hollow body; positioning a second anastomotic component on the delivery device, the second anastomotic component adapted to be secured to a second hollow body, wherein the first and second anastomotic components are magnetically attracted to each other and are positioned on the delivery device in an offset configuration with respect to one another; securing the second anastomotic component to a second hollow body so as to place the opening of the second component in communication with the second hollow body; moving the first and second anastomotic components from the offset configuration into substantial alignment with each other; and using magnetism to couple the first and second anastomotic components and form an anastomosis between the first and second hollow bodies.

26. The method of claim 25, wherein magnetic attraction between the delivery device and at least one of the first and second anastomotic components is used to move the components from the offset configuration.

27. A method for coupling first and second magnetically attracted anastomotic components, the method comprising steps of: receiving at least first and second anastomotic components configured to be secured to a first hollow body, the first and second components being magnetically attracted to one another; providing a delivery device; mounting the first anastomotic component on the delivery device; mounting the second anastomotic component on the delivery device; and using magnetic repulsion between a portion of the delivery device and the first anastomotic component to move the first anastomotic component toward the second anastomotic component.

28. The method of claim 27, wherein the delivery device includes a permanent magnet oriented to repel the first anastomotic component.

29. The method of claim 27, wherein only the first and second anastomotic components are mounted on the delivery device.

* * * * *